US011583571B2

(12) United States Patent
Sopko et al.

(10) Patent No.: US 11,583,571 B2
(45) Date of Patent: Feb. 21, 2023

(54) STROMAL DERIVED FACTOR 1 AND ITS USE IN THE PREVENTION AND TREATMENT OF ERECTILE DYSFUNCTION

(71) Applicants: THE JOHNS HOPKINS UNIVERSITY, Baltimore, MD (US); SUMMA HEALTH SYSTEM, Akron, OH (US)

(72) Inventors: Nikolai Sopko, Baltimore, MD (US); Trinity Bivalacqua, Baltimore, MD (US); Marc Penn, Akron, OH (US)

(73) Assignees: The Johns Hopkins University, Baltimore, MD (US); Summa Health System, Akron, OH (US)

( * ) Notice: Subject to any disclaimer, the term of this patent is extended or adjusted under 35 U.S.C. 154(b) by 0 days.

(21) Appl. No.: 16/613,282

(22) PCT Filed: May 11, 2018

(86) PCT No.: PCT/US2018/032265
§ 371 (c)(1),
(2) Date: Nov. 13, 2019

(87) PCT Pub. No.: WO2018/213125
PCT Pub. Date: Nov. 22, 2018

(65) Prior Publication Data
US 2020/0188483 A1 Jun. 18, 2020

Related U.S. Application Data

(60) Provisional application No. 62/505,864, filed on May 13, 2017.

(51) Int. Cl.
| A61K 38/19 | (2006.01) |
| A61P 15/10 | (2006.01) |
| A61K 9/00 | (2006.01) |
| A61K 38/18 | (2006.01) |
| A61K 45/06 | (2006.01) |

(52) U.S. Cl.
CPC .......... *A61K 38/195* (2013.01); *A61K 9/0019* (2013.01); *A61K 38/185* (2013.01); *A61K 45/06* (2013.01); *A61P 15/10* (2018.01)

(58) Field of Classification Search
None
See application file for complete search history.

(56) References Cited

U.S. PATENT DOCUMENTS

| 8,513,007 B2 | 8/2013 | Penn et al. |
| 8,679,477 B2 | 3/2014 | Penn et al. |
| 2010/0272679 A1 | 10/2010 | Penn et al. |
| 2014/0081012 A1* | 3/2014 | DeSimone ........... C07D 207/46 536/24.5 |
| 2016/0024521 A1 | 1/2016 | Penn et al. |

FOREIGN PATENT DOCUMENTS

| SG | WO 2015/084264 | * 6/2015 | ........... C07K 14/575 |
| WO | WO 99/11655 | * 3/1999 | ............... C07K 1/04 |
| WO | WO 2007/149548 | * 12/2007 | ............... C12N 5/00 |
| WO | 2009046446 A2 | 4/2009 | |
| WO | 2012037083 A2 | 3/2012 | |

OTHER PUBLICATIONS

Bhattacharya et al., PLoS ONE 12(3): e0171355. https://doi.org/10.1371/journal.pone.0171355; 22 pages total (Year: 2017).*
Fenton et al., Medicinal Chemistry Research (2020) 29:1133-1146 (Year: 2020).*
Mishra et al., Scientific Reports, published Jul. 26, 2016, 6:30155; doi: 10.1038/srep30155; 9 pages total (Year: 2016).*
The abstract by Sopko et al., Eur Urol Suppl Mar. 2016;15(3);e887 (Year: 2016).*
Lin et al. International Journal of Impotence Research (2004) 16, S38-S39 (Year: 2004).*
Bertrand and Keast, "Dissection of Pelvic Autonomic Ganglia and Associated Nerves in Male and Female Rats" in J. Vis. Exp. (157), e60904, doi:10.3791/60904 (2020) (Year: 2020).*
Yucel et al., Asian J Androl 2005; 7 (4): 339-349 (Year: 2005).*
Sopko, et al., Understanding and Targeting the Rho Kinase Pathway in Erectile Dysfunction. Nature Reviews Urology 2014, 11, 622-628.
Sopko, et al., Erection rehabilitation following prostatectomy—current strategies and future directions. Nature Reviews Urology 2016, 13, 216-225.
Hannah, et al., Caspase-3 dependent nitrergic neuronal apoptosis following cavernous nerve injury is mediated via RhoA and ROCK activation in major pelvic ganglion. Scientific Reports 2016, 6, 29416.
Nagasawa, et al., Molecular cloning and structure of a pre-B-cell growth-stimulating factor. Proceedings of the National Academy of Sciences of the United States of America 1994, 91, 2305-2309.
Keddie, et al., RNA-binding protein Dnd1 inhibits microRNA access to target mRNA. Cell 2007, 131, 1273-1286.

(Continued)

*Primary Examiner* — Christina M Borgeest
(74) *Attorney, Agent, or Firm* — DLA Piper LLP (US)

(57) ABSTRACT

Stromal Derived Factor-1 (SDF-1) is a small, naturally occurring, potent chemokine with inherent angiogenic, neurogenic, anti-apoptotic protein, which is also a potent stem cell chemoattractant, cardiovascular disease, and other metabolic disturbances. The present invention provides methods for treating erectile dysfunction in a male subject comprising administering to the major pelvic ganglion supplying the cavernous nerves subject compositions comprising SDF-1. SDF-1 promotes stem cell activation, to the major pelvic ganglion supplying the cavernous nerves, helps cell preservation, and prevents adverse penile remodeling. It can be administered as a protein or by gene therapy including but not limited to plasmid DNA, viral transduction, or nanoparticle delivery directly to the penis or to the neurovascular bundle or other pelvic nerve structures during the time of surgery, or before injury, or to treat existing erectile dysfunction.

10 Claims, 21 Drawing Sheets

Specification includes a Sequence Listing.

(56) References Cited

OTHER PUBLICATIONS

Penn, et al., An Open Label Dose Escalation Study to Evaluate the Safety of AminisliaLion of Non-Viral SDF-1 Plasmid to Treat Symptomatic Ischemic Heart Failure. Circulation Research 2013, 112, 816-825.

Weyne, et al., Decade in review—sexual dysfunction: Post-RP erectile dysfunction—therapies for the next decade. Nature Reviews Urology, 2014, 11, 616-618.

Hakim, et al., Emerging tools for erectile dysfunction: a role for regenerative medicine. Nature Reviews Urology, 2012, 9, 520-536.

Yu, L., et al., "Identification and expression of novel isoforms of human stromal cell-derived factor 1" Gene 374 (2006) 174-179.

Shan, H., et al., "Combination of low-energy shock-wave therapy and bone marrow mesenchymal stem cell transplantation to improve the erectile function of diabetic rats" Asian Journal of Andrology (2017) 19, 26-33.

Fandel, T., et al., "Recruitment of Intracavernously Injected Adipose-Derived Stem Cells to the Major Pelvic Ganglion Improves Erectile Function in a Rat Model of Cavernous Nerve Injury" Eur Urol. Jan. 2012 ; 61(1): 201-210. doi:10.1016/j.eururo.2011.07.061.

\* cited by examiner

FIGURE 1A

```
   1 tctccgtcag ccgcattgcc cgctcggcgt ccggccccg acccgtgctc gtccgcccgc
  61 ccgcccgccc gcccgcgcca tgaacgccaa ggtcgtggtc gtgctggtcc tcgtgctgac
 121 cgcgctctgc ctcagcgacg ggaagcccgt cagcctgagc tacagatgcc catgccgatt
 181 cttcgaaagc catgttgcca gagccaacgt caagcatctc aaaattctca acactccaaa
 241 ctgtgccctt cagattgtag cccggctgaa gaacaacaac agacaagtgt gcattgaccc
 301 gaagctaaag tggattcagg agtacctgga gaaagcttta aacaagaggt tcaagatgtg
 361 agagggtcag acgcctgagg aaccctaca gtaggagccc agctctgaaa ccagtgttag
 421 ggaagggcct gccacagcct ccctgccag ggcagggccc caggcattgc caaggctttt
 481 gttttgcaca ctttgccata ttttcaccat ttgattatgt agcaaaatac atgacattta
 541 tttttcattt agtttgatta ttcagtgtca ctggcgacac gtagcagctt agactaaggc
 601 cattattgta cttgccttat tagagtgtct ttccacggag ccactcctct gactcagggc
 661 tcctgggttt tgtattctct gagctgtgca ggtggggaga ctgggctgag ggagcctggc
 721 cccatggtca gccctagggt ggagagccac caagagggac gcctgggggt gccaggacca
 781 gtcaacctgg gcaaagccta gtgaaggctt ctctctgtgg gatgggatgg tggagggcca
 841 catgggaggc tcaccccctt ctccatccac atgggagccg ggtctgcctc ttctgggagg
 901 gcagcagggc taccctgagc tgaggcagca gtgtgaggcc agggcagagt gagacccagc
 961 cctcatcccg agcacctcca catcctccac gttctgctca tcattctctg tctcatccat
1021 catcatgtgt gtccacgact gtctccatgg cccgcaaaa ggactctcag gaccaaagct
1081 ttcatgtaaa ctgtgcacca agcaggaaat gaaatgtct tgtgttacct gaaaacactg
1141 tgcacatctg tgtcttgtgt ggaatattgt ccattgtcca atcctatgtt tttgttcaaa
1201 gccagcgtcc tcctctgtga ccaatgtctt gatgcatgca ctgttccccc tgtgcagccg
1261 ctgagcgagg agatgctcct tgggcccttt gagtgcagtc ctgatcagag ccgtggtcct
1321 ttggggtgaa ctaccttggt tcccccactg atcacaaaaa catggtgggt ccatgggcag
1381 agccaaggg aattcggtgt gcaccaggt tgaccccaga ggattgctgc cccatcagtg
1441 ctccctcaca tgtcagtacc ttcaaactag ggcaagccc agcactgctt gaggaaaaca
1501 agcattcaca acttgttttt ggttttaaa acccagtcca caaataacc aatcctggac
1561 atgaagattc tttcccaatt cacatctaac ctcatcttct tcaccatttg gcaatgccat
1621 catctcctgc cttcctcctg ggccctctct gctctgcgtg tcacctgtgc ttcgggccct
1681 tcccacagga catttctcta agagaacaat gtgctatgtg aagagtaagt caacctgcct
1741 gacatttgga gtgttcccct cccactgagg gcagtcgata gagctgtatt aagccactta
1801 aaatgttcac ttttgacaaa ggcaagcact tgtgggtttt tgttttgttt ttcattcagt
1861 cttacgaata cttttgccct ttgattaaag actccagtta aaaaaaattt taatgaagaa
1921 agtggaaaac aaggaagtca aagcaaggaa actatgtaac atgtaggaag taggaagtaa
1981 attatagtga tgtaatcttg aattgtaact gttcgtgaat ttaataatct gtagggtaat
2041 tagtaacatg tgttaagtat tttcataagt atttcaaatt ggagcttcat ggcagaaggc
2101 aaacccatca acaaaaattg tcccttaaac aaaattaaa atcctcaatc cagctatgtt
2161 atattgaaaa aatagagcct gagggatctt tactagttat aaagatacag aactcttcca
2221 aaaccttttg aaattaacct ctcactatac cagtataatt gagttttcag tggggcagtc
2281 attatccagg taatccaaga tattttaaaa tctgtcacgt agaacttgga tgtacctgcc
2341 cccaatccat gaaccaagac cattgaattc ttggttgagg aaacaaacat gaccctaaat
2401 cttgactaca gtcaggaaag gaatcatttc tatttctcct ccatgggaga aaatagataa
2461 gagtagaaac tgcagggaaa attatttgca taacaattcc tctactaaca atcagctcct
2521 tcctggagac tgcccagcta aagcaatatg catttaaata cagtcttcca tttgcaaggg
2581 aaaagtctct tgtaatccga atctcttttt gctttcgaac tgctagtcaa gtgcgtccac
2641 gagctgttta ctagggatcc ctcatctgtc cctccgggac ctggtgctgc ctctacctga
2701 cactcccttg ggctccctgt aacctcttca gaggccctcg ctgccagctc tgtatcagga
2761 cccagaggaa ggggccagag gctcgttgac tggctgtgtg ttgggattga gtctgtgcca
2821 cgtgtatgtg ctgtggtgtg tccccctctg tccaggcact gagataccag cgaggaggct
2881 ccagagggca ctctgcttgt tattagagat tacctcctga gaaaaagct tccgcttgga
2941 gcagaggggc tgaatagcag aaggttgcac ctcccccaac cttagatgtt ctaagtcttt
3001 ccattggatc tcattggacc cttccatggt gtgatcgtct gactggtgtt atcaccgtgg
3061 gctccctgac tgggagttga tcgcctttcc caggtgctac acccttttcc agctggatga
3121 gaatttgagt gctctgatcc ctctacagag cttccctgac tcattctgaa ggagccccat
3181 tcctgggaaa tattccctag aaacttccaa atcccctaag cagaccactg ataaaaccat
3241 gtagaaaatt tgttattttg caacctcgct ggactctcag tctctgagca gtgaatgatt
3301 cagtgttaaa tgtgatgaat actgtatttt gtattgtttc aagtgcatct cccagataat
3361 gtgaaaatgg tccaggagaa ggccaattcc tatacgcagc gtgctttaaa aaataaataa
3421 gaaacaactc tttgagaaac aacaatttct actttgaagt cataccaatg aaaaaatgta
```

FIGURE 1B

```
3481 tatgcactta taattttcct aataaagttc tgtactcaaa tgta (SEQ ID NO: 2)
``` n = 5/group, *P < 0.05 compared to control

TIME 0

SEQUENCE LISTING

```
<160> NUMBER OF SEQ ID NOS: 2

<210> SEQ ID NO 1
<211> LENGTH: 93
<212> TYPE: PRT
<213> ORGANISM: Mus musculus

<400> SEQUENCE: 1

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
                35                  40                  45

Ile Leu Asn Thr Pro Asn Cys Ala Leu Gln Ile Val Ala Arg Leu Lys
            50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90

<210> SEQ ID NO 2
<211> LENGTH: 3524
<212> TYPE: DNA
<213> ORGANISM: Mus musculus

<400> SEQUENCE: 2
tctccgtcag ccgcattgcc cgctcggcgt ccggccccg acccgtgctc gtccgcccgc       60
ccgcccgccc gcccgcgcca tgaacgccaa ggtcgtggtc gtgctggtcc tcgtgctgac      120
cgcgctctgc ctcagcgacg ggaagcccgt cagcctgagc tacagatgcc catgccgatt      180
cttcgaaagc catgttgcca gagccaacgt caagcatctc aaaattctca acactccaaa      240
ctgtgccctt cagattgtag cccggctgaa gaacaacaac agacaagtgt gcattgaccc      300
gaagctaaag tggattcagg agtacctgga gaaagcttta aacaagaggt tcaagatgtg      360
agagggtcag acgcctgagg aacccttaca gtaggagccc agctctgaaa ccagtgttag      420
ggaagggcct gccacagcct ccctgccag gcagggccc caggcattgc caagggcttt       480
gttttgcaca ctttgccata ttttcaccat ttgattatgt agcaaaatac atgacattta      540
tttttcattt agtttgatta ttcagtgtca ctggcgacac gtagcagctt agactaaggc      600
cattattgta cttgccttat tagagtgtct ttccacggag ccactcctct gactcagggc      660
tcctgggttt tgtattctct gagctgtgca ggtggggaga ctgggctgag ggagcctggc      720
cccatggtca gccctagggt ggagagccac caagaggac gcctgggggt gccaggacca       780
gtcaacctgg gcaaagccta gtgaaggctt ctctctgtgg gatgggatgg tggagggcca      840
catgggaggc tcaccccctt ctccatccac atgggagccg ggtctgcctc ttctgggagg      900
```

```
gcagcagggc taccctgagc tgaggcagca gtgtgaggcc agggcagagt gagacccagc    960
cctcatcccg agcacctcca catcctccac gttctgctca tcattctctg tctcatccat   1020
catcatgtgt gtccacgact gtctccatgg ccccgcaaaa ggactctcag gaccaaagct   1080
ttcatgtaaa ctgtgcacca agcaggaaat gaaaatgtct tgtgttacct gaaaacactg   1140
tgcacatctg tgtcttgtgt ggaatattgt ccattgtcca atcctatgtt tttgttcaaa   1200
gccagcgtcc tcctctgtga ccaatgtctt gatgcatgca ctgttccccc tgtgcagccg   1260
ctgagcgagg agatgctcct tgggcccttt gagtgcagtc ctgatcagag ccgtggtcct   1320
ttggggtgaa ctaccttggt tcccccactg atcacaaaaa catggtgggt ccatgggcag   1380
agcccaaggg aattcggtgt gcaccagggt tgaccccaga ggattgctgc cccatcagtg   1440
ctccctcaca tgtcagtacc ttcaaactag ggccaagccc agcactgctt gaggaaaaca   1500
agcattcaca acttgttttt ggttttaaaa acccagtcca caaaataacc aatcctggac   1560
atgaagattc tttcccaatt cacatctaac ctcatcttct tcaccatttg gcaatgccat   1620
catctcctgc cttcctcctg ggccctctct gctctgcgtg tcacctgtgc ttcgggccct   1680
tcccacagga catttctcta agagaacaat gtgctatgtg aagagtaagt caacctgcct   1740
gacatttgga gtgttcccct cccactgagg gcagtcgata gagctgtatt aagccactta   1800
aaatgttcac ttttgacaaa ggcaagcact tgtgggtttt tgttttgttt ttcattcagt   1860
cttacgaata cttttgccct ttgattaaag actccagtta aaaaaatttt taatgaagaa   1920
agtggaaaac aaggaagtca aagcaaggaa actatgtaac atgtaggaag taggaagtaa   1980
attatagtga tgtaatcttg aattgtaact gttcgtgaat ttaataatct gtagggtaat   2040
tagtaacatg tgttaagtat tttcataagt atttcaaatt ggagcttcat ggcagaaggc   2100
aaacccatca acaaaaattg tcccttaaac aaaaattaaa atcctcaatc cagctatgtt   2160
atattgaaaa aatagagcct gagggatctt tactagttat aaagatacag aactctttca   2220 aaacctttg aaattaacct ctcactatac cagtataatt gagttttcag tggggcagtc   2280
attatccagg taatccaaga tattttaaaa tctgtcacgt agaacttgga tgtacctgcc   2340
cccaatccat gaaccaagac cattgaattc ttggttgagg aaacaaacat gaccctaaat   2400
cttgactaca gtcaggaaag gaatcatttc tatttctcct ccatgggaga aaatagataa   2460
gagtagaaac tgcagggaaa attatttgca taacaattcc tctactaaca atcagctcct   2520
tcctggagac tgcccagcta agcaatatg catttaaata cagtcttcca tttgcaaggg   2580
aaaagtctct tgtaatccga atctcttttt gctttcgaac tgctagtcaa gtgcgtccac   2640
gagctgttta ctagggatcc ctcatctgtc cctccgggac ctggtgctgc ctctacctga   2700
cactcccttg ggctccctgt aacctcttca gaggccctcg ctgccagctc tgtatcagga   2760
cccagaggaa ggggccagag gctcgttgac tggctgtgtg ttgggattga gtctgtgcca   2820
cgtgtatgtg ctgtggtgtg tcccctctg tccaggcact gagataccag cgaggaggct   2880
ccagagggca ctctgcttgt tattagagat tacctcctga gaaaaagct tccgcttgga   2940 gcagagggc tgaatagcag aaggttgcac ctcccccaac cttagatgtt ctaagtcttt   3000
ccattggatc tcattggacc cttccatggt gtgatcgtct gactggtgtt atcaccgtgg   3060
gctccctgac tgggagttga tcgccttttcc caggtgctac acccttttcc agctggatga   3120
gaatttgagt gctctgatcc ctctacagag cttccctgac tcattctgaa ggagccccat   3180
tcctgggaaa tattccctag aaacttccaa atcccctaag cagaccactg ataaaaccat   3240
gtagaaaatt tgttattttg caacctcgct ggactctcag tctctgagca gtgaatgatt   3300
```

```
cagtgttaaa tgtgatgaat actgtatttt gtattgtttc aagtgcatct cccagataat    3360
gtgaaaatgg tccaggagaa ggccaattcc tatacgcagc gtgctttaaa aaataaataa    3420
gaaacaactc tttgagaaac aacaatttct actttgaagt cataccaatg aaaaaatgta    3480
tatgcactta taattttcct aataaagttc tgtactcaaa tgta                     3524
```

US 11,583,571 B2

STROMAL DERIVED FACTOR 1 AND ITS USE IN THE PREVENTION AND TREATMENT OF ERECTILE DYSFUNCTION

CROSS-REFERENCE TO RELATED APPLICATIONS

This application is a 35 U.S.C. § 371 U.S. national entry of International Application PCT/US2018/032265, having an international filing date of May 11, 2018, which claims the benefit of U.S. Provisional Application No. 62/505,864, filed May 13, 2017, the content of each of the aforementioned applications is herein incorporated by reference in their entirety.

STATEMENT OF GOVERNMENTAL INTEREST

This invention was made with government support under DK090370, awarded by the National Institutes of Health. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on May 13, 2017, is named P14408-01_ST25.txt and is 5,803 bytes in size.

BACKGROUND OF THE INVENTION

Stromal derived factor 1 (SDF-1) is a small (110 KD), highly conserved chemokine. Discovered in the early 1990's as being important for bone marrow homing and B-cell proliferation. It is also known as chemokine (C—X—C motif) ligand 12", SDF1, SDF1A, 1B, PBSF, SCYB12, SDF-1a, SDF-1b, TLSF-a, TLSF-b, and TPAR1. A stromal cell-derived alpha chemokine member of the intercrine family. The encoded protein functions as the ligand for the G-protein coupled receptor, chemokine (C—X—C motif) receptor 4, and plays a role in many diverse cellular functions, including embryogenesis, immune surveillance, inflammation response, tissue homeostasis, and tumor growth and metastasis. Mutations in this gene are associated with resistance to human immunodeficiency virus type 1 infections. Multiple transcript variants encoding different isoforms have been found for this gene. Plerixafor (AMD-3100), used to mobilize hematopoietic stem cells for isolation prior to bone marrow transplantation is an antagonistic inhibitor of CXCR4. SDF-1 is unregulated in many tissues (i.e. heart, brain, muscle) following injury, especially ischemic injury.

Erectile dysfunction is a male sexual dysfunction characterized by the inability to develop or maintain an erection of the penis during sexual intercourse. There are two major causes for erectile dysfunction: psychogenic and organic causes. The psychogenic cause is attributed to the activation of sympathetic nervous system and inhibition of non-adrenergic-non-cholinergic nerve system by psychological or mental effect, which elicits an increase in the smooth muscle tension of corpus cavernosum (erectile tissue of the penis) and resultant erectile dysfunction. The organic erectile dysfunctions are divided into neurogenic, vasculogenic, and endocrine erectile dysfunctions according to the cause.

The vasculogenic erectile dysfunction is known to cause insufficient secretion of relaxation neurotransmitters (e.g., nitric oxide (NO)) from cavernous endothelial cells due to endothelial dysfunction that are caused by hyperlipidemia, diabetes mellitus, high blood pressure, smoking, metabolic syndrome, other vascular risk factors, etc.

Recent researches associated with erectile dysfunction have intensely focused on the organic erectile dysfunction. Phosphodiesterase-5 (PDE-5) inhibitors for oral administration including Viagra (Sildenafil's trade name) are widely utilized as first-line therapy for erectile dysfunction. Oral PDE-5 inhibitors are well known to be effective for the treatment of erectile dysfunction by potentiating the physiologic erectile response to NO and by amplifying the NO-cyclic GMP pathway through competitive inhibition of cyclic GMP degradation.

However, more than 30% of total patients with erectile dysfunction, including diabetic patients, those with spinal cord injuries and those who underwent radical prostatectomy for the treatment for prostatic cancer, etc., do not respond to oral PDE-5 inhibitors.

Prostate surgery results in a temporary neuropraxia resulting in near complete temporary loss of erectile function resulting in decreased penile tissue perfusion. More seriously injured nerves undergo Wallerian degeneration resulting in loss in penile tissue innervation. Morphological tissue changes include smooth muscle apoptosis, decreased density of microvasculature, increased collagen/scar remodeling and replacement of erectile tissues seen both in humans and in animals (using the cavernous nerve crush model). Furthermore, these injuries result in Aberrant molecular signaling including increased RhoA/ROCK activation, decreased nNOS, increased free radical production, decreased growth factor expression.

Moreover, adverse events associated with PDE-5 inhibitor treatment such as headache, facial flushing, indigestion, back pain/myalgia, visual disturbance are not infrequent. In addition, these treatments have also some restrictions in their application. PDE-5 inhibitors are absolutely contraindicated for patients using nitrates and are either not recommended or to be used with caution in men with severe cardiovascular disease such as unstable angina, cardiac failure, recent myocardial infarct, poorly controlled blood pressure, in men who takes ketokonazole, itraconazole, ritonavir, alpha-adrenergic blocker, and in patients with severe hepatic insufficiency or renal insufficiency, etc. Furthermore, PDE5 inhibitors are used as on demand medicines but not effective to cure underlying disease at all, which limits the spontaneity of the sexual activity and causes higher drop out rate of the treatment.

SUMMARY OF THE INVENTION

In accordance with an embodiment, the present invention provides methods for increasing neuronal growth and neuronal preservation in the pelvic ganglion neurons, neurovascular bundles and cavernous nervous tissue in a subject comprising administering to the penile tissue of the subject, an effective amount of a composition comprising SDF-1; b) a functional fragment of a); c) a functional homolog of a) or b) or functional fragment thereof; and d) a fusion polypeptide comprising an amino acid sequence of any of a) to c), or a nucleotide sequence that results in expression of a protein product relating to a), b), or c).

In accordance with an embodiment, the present invention provides methods for increasing neuronal growth in peripheral parasympathetic nervous tissue in a subject comprising administering to the penile tissue of the subject, an effective amount of a composition comprising SDF-1; b) a functional fragment of a); c) a functional homolog of a) or b) or functional fragment thereof; and d) a fusion polypeptide comprising an amino acid sequence of any of a) to c), or a nucleotide sequence that results in expression of a protein product relating to a), b), or c).

In accordance with another embodiment, the present invention provides methods for treating erectile dysfunction in a subject suffering therefrom comprising administering to the penile tissue of the subject, an effective amount of a composition comprising SDF-1; b) a functional fragment of a); c) a functional homolog of a) or b) or functional fragment thereof; and d) a fusion polypeptide comprising an amino acid sequence of any of a) to c).

In accordance with another embodiment, the present invention provides methods for preserving erectile function and preventing erectile dysfunction in a subject undergoing prostate surgery comprising administering to the penile tissue (and/or neurovascular bundle) of the subject, an effective amount of a composition comprising SDF-1; b) a functional fragment of a); c) a functional homolog of a) or b) or functional fragment thereof; and d) a fusion polypeptide comprising an amino acid sequence of any of a) to c).

BRIEF DESCRIPTION OF THE DRAWINGS

FIGS. 1A-1B show a DNA sequence for SDF-1A.

DETAILED DESCRIPTION OF THE INVENTION

Figure 2:
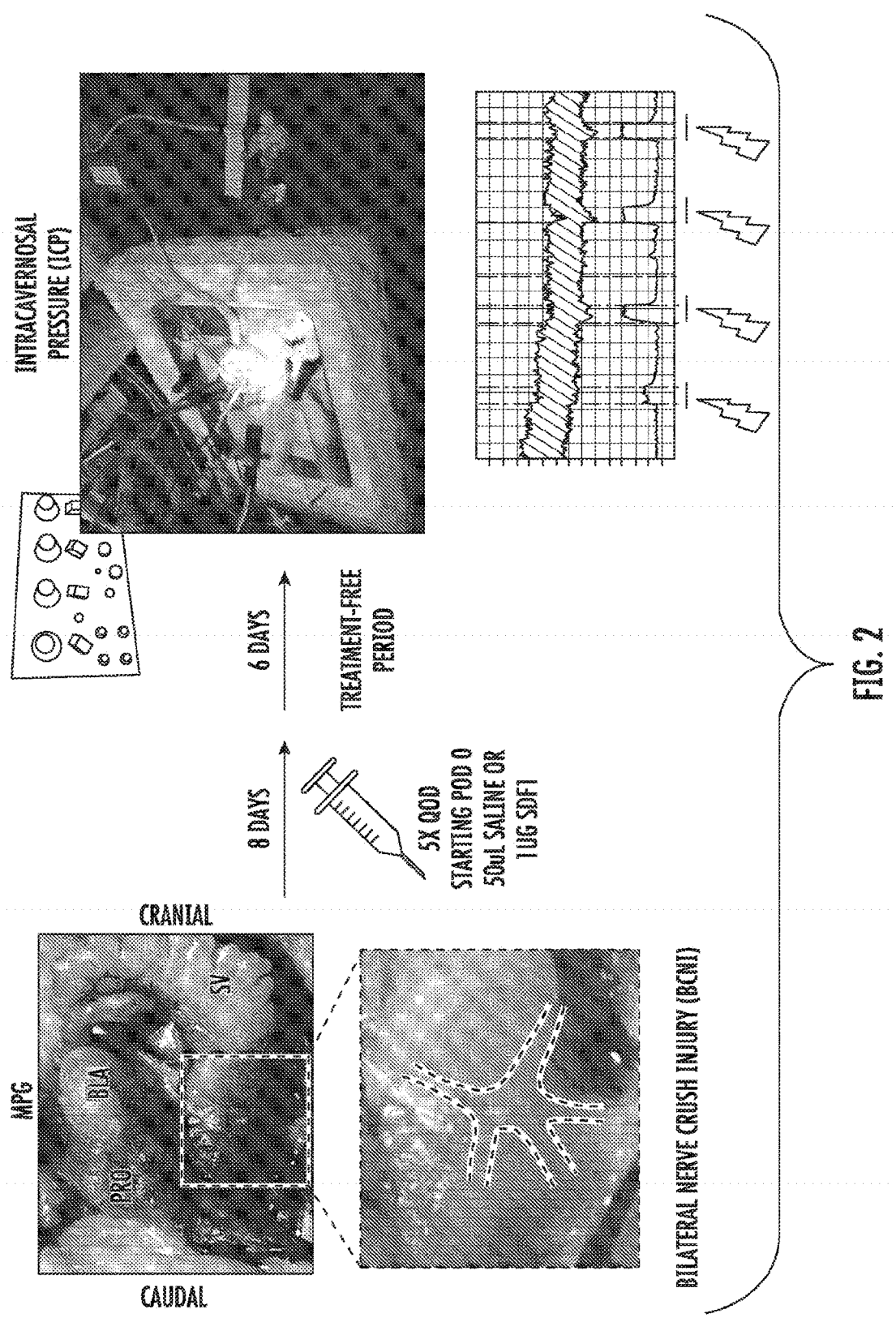
FIG. 2 is a schematic of a rat based model for erectile dysfunction, the bilateral nerve crush injury (BCNI). The right panels show the gross anatomy of the rat major pelvic ganglion and an enlarged area showing the injury area. The left panels show the apparatus used for measurement of the intracavernosal pressure (ICP) in the penile tissue of the rat and the pressure tracings (mean arterial pressure in red tracing) showing an increase in intracavernosal pressure (blue lower tracing) with electrical stimulation of the cavernous nerve.

SDF-1 is a peptide with accession number NM_000609 and has many orthologs. The gene which encodes SDF-1 comprises a 3549 bp mRNA, which is shown in FIG. 1. One particular variant of the peptide has the following sequence: MNAKVVVVLVLVLTALCLSDGKPVSLSYRCPCRF-FESHVARANVKHLKILNTPNCA LQIVARLKNNNRQV-CIDPKLKWIQEYLEKALNKRFKM (SEQ ID NO: 1). There are two major isoforms, 1A and 1B, with 1B longer of the two. There are several isoforms of SDF1: (SDF-1alpha, SDF-1beta, SDF-1gamma, SDF-1delta, SDF-1 epsilon and SDF-1phi). The n-terminus of the protein is the same between all of them and is what binds to its receptor cxcr4 but they differ in the c-terminus, which is where breakdown of the protein occurs so the other isoforms are hypothesized to be more stable than alpha. Alpha is the most predominant isoform in the body and the vast majority of research and therapeutics has focused on SDF-1a.

In accordance with an embodiment, the present invention provides methods for increasing neuronal growth in major pelvic ganglions and cavernous nervous tissue as well as promoting beneficial penile tissue architecture such as smooth muscle and vascular function in a subject comprising administering to the penile tissue of the subject, an effective amount of a composition comprising SDF-1; b) a functional fragment of a); c) a functional homolog of a) or b) or functional fragment thereof; and d) a fusion polypeptide comprising an amino acid sequence of any of a) to c) or a nucleotide sequence that results in expression of a protein product relating to a), b), or c).

It will be understood by those of skill in the art, that the methods and compositions of the present invention can include any and all of the variants of SDF-1 and analogs and truncations as well.

As used herein the term "major pelvic ganglion" comprises the large numbers of the postganglionic neurons which innervate the pelvic organs are located in the major pelvic ganglion and neurovascular bundle. Within this ganglion, the neurons project to either of three pelvic organs, the penis, colon or urinary bladder. Most of the colon neurons are located in the major pelvic ganglion near the entrance of the pelvic nerve, whereas almost all of the penis neurons are near or within the penile nerve. Bladder neurons are relatively evenly distributed throughout the ganglion.

The Major Pelvic Ganglion is the anatomical structure targeted in rats in accordance with the present invention, which is the analogue to the 'Pelvic Ganglion' in humans. However, in humans the neurovascular bundle surrounding the prostate, which arises from the pelvic ganglion is what is injured during surgery and is what the present invention will be targeting by intra-operative SDF-1 treatment. So use of the term "major pelvic ganglion" is interchangable with "pelvic ganglion" or "neurovascular bundle" when used in context of human treatment. The neurovascular bundle comprises the nerves that are 'spared' during a nerve-sparing prostatectomy.

As used herein the term "penile tissue" means generally the tissues associated with the structure and function of the penis, including, for example, the root, Crus, Bulb, Fundiform ligament, Suspensory ligament, body, Corpus cavernosum, Corpus spongiosum, glans, Foreskin, Frenulum, Corona, fascia, Tunica albuginea, Septum of the penis, Internal urethral orifice, Urethra (Prostatic, Intermediate, Spongy), Navicular fossa, External urethral orifice, Lacunae of Morgagni, the Urethral gland, and neighboring genitourinary tissues.

Without being held to any particular theory, the term "increasing neuronal growth in major pelvic ganglions and cavernous nervous tissue" in a subject means enhancement of axon elongation via SDF-1 binding to its receptor CXCR4, and thereby upregulating neurotrophic growth factors. Such growth factors include, but are not limited to BDNF, bFGF, BMP4, EGFR, EG-VEGF, FGF-7, GH, IGFBP-2, IGF-1, and PDGβ-AA.

In accordance with an embodiment, the present invention provides methods for increasing neuronal growth in peripheral parasympathetic nervous tissue in a subject comprising administering to the penile tissue of the subject, an effective amount of SDF-1; b) a functional fragment of a); c) a functional homolog of a) or b) or functional fragment thereof; and d) a fusion polypeptide comprising an amino acid sequence of any of a) to c).

In accordance with another embodiment, the present invention provides for the use of an effective amount of a composition comprising SDF-1; b) a functional fragment of a); c) a functional homolog of a) or b) or functional fragment thereof; and d) a fusion polypeptide comprising an amino acid sequence of any of a) to c) for treating erectile dysfunction in a subject suffering therefrom.

In accordance with another embodiment, the present invention provides for the use of an effective amount of a composition comprising SDF-1; b) a functional fragment of a); c) a functional homolog of a) or b) or functional fragment thereof; and d) a fusion polypeptide comprising an amino acid sequence of any of a) to c) for preventing erectile dysfunction in a subject undergoing prostate surgery.

In accordance with another embodiment, the present invention provides for the use of an effective amount of a composition comprising SDF-1; b) a functional fragment of a); c) a functional homolog of a) or b) or functional fragment thereof; and d) a fusion polypeptide comprising an amino acid sequence of any of a) to c), for increasing beneficial penile architecture and neuronal growth in the neurovascular bundle and cavernous nervous tissue in a subject in need thereof.

In accordance with another embodiment, the present invention provides for the use of an effective amount of a composition comprising SDF-1; b) a functional fragment of a); c) a functional homolog of a) or b) or functional fragment thereof; and d) a fusion polypeptide comprising an amino acid sequence of any of a) to c) for increasing beneficial penile architecture and neuronal growth in peripheral parasympathetic nervous tissue in a subject in need thereof.

As used herein the term "increasing neuronal growth in peripheral parasympathetic nervous tissue" means that SDF-1 treatment provides neurogenic properties to the tissues which are responsible for relaxation signaling required for erections. These nerves are injured both during surgery and from organic causes of erectile dysfunction including diabetes and cardiovascular disease. In some embodiments, the increased neuronal growth means increased erectile and sexual function when compared to control or untreated damaged nerves or pre-surgical function.

Reference herein to "derivatives" includes parts, fragments and portions of the SDF-1 peptides. A derivative also includes a single or multiple amino acid substitution, deletion and/or addition. Homologues include functionally, structurally or stereochemically similar peptides including orthologs, splice variants and the like. All such homologues are contemplated by the present invention. Also included in the compositions and methods provided herein are peptide analogs with like-characteristic amino acid substitutions. For example, substitution of one or more neutral or non-polar amino acid for another, or a positively charged amino acid for another, hydrophobic for hydrophobic, etc.

Analogs and mimetics include molecules which include molecules which contain non-naturally occurring amino acids or which do not contain amino acids but nevertheless behave functionally the same as the peptide. Natural product screening is one useful strategy for identifying analogs and mimetics.

The term, "amino acid" includes the residues of the natural a-amino acids (e.g., Ala, Arg, Asn, Asp, Cys, Glu, Gln, Gly, His, Lys, Ile, Leu, Met, Phe, Pro, Ser, Thr, Trp, Tyr, and Val) in D or L form, as well as β-amino acids, synthetic and non-natural amino acids. Many types of amino acid residues are useful in the polypeptides and the invention is not limited to natural, genetically-encoded amino acids. Examples of amino acids that can be utilized in the peptides described herein can be found, for example, in Fasman, 1989, CRC Practical Handbook of Biochemistry and Molecular Biology, CRC Press, Inc., and the reference cited therein. Another source of a wide array of amino acid residues is provided by the website of RSP Amino Acids LLC.

Examples of incorporating non-natural amino acids and derivatives during peptide synthesis include, but are not limited to, use of norleucine, 4-amino butyric acid, 4-amino- 3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A partial list of known non-natural amino acid contemplated herein is shown in Table 1.

TABLE 1

Non-natural Amino Acids

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |

TABLE 1-continued

Non-natural Amino Acids

| Non-conventional amino acid | Code | Non-conventional amino acid | Code |
|---|---|---|---|
| L-t-butylglycine | Thug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Analogs of the subject peptides contemplated herein include modifications to side chains, incorporation of non-natural amino acids and/or their derivatives during peptide synthesis and the use of cross-linkers and other methods which impose conformational constraints on the peptide molecule or their analogs.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of Cα and Nα-methylamino acids, introduction of double bonds between Cα and Cβ atoms of amino acids and the formation of cyclic peptides or analogues by introducing covalent bonds such as forming an amide bond between the N and C termini, between two side chains or between a side chain and the N or C terminus.

The term, "peptide," as used herein, includes a sequence of from four to 100 amino acid residues in length, preferably about 10 to 95 residues in length, more preferably, 15 to 90 residues in length, and in which the α-carboxyl group of one amino acid is joined by an amide bond to the main chain (α- or β-) amino group of the adjacent amino acid. The peptides provided herein for use in the described and claimed methods and compositions can also be cyclic.

The precise effective amount for a human subject will depend upon the severity of the subject's disease state, general health, age, weight, gender, diet, time and frequency of administration, drug combination(s), reaction sensitivities, and tolerance or response to therapy. A routine experimentation can determine this amount and is within the judgment of the medical professional. Compositions may be administered individually to a patient, or they may be administered in combination with other drugs, hormones, agents, and the like.

Routes of administration of the inventive peptides and nucleotides include, but are not limited to intravenously, intraperitioneal, subcutaneously, intradermal, intramuscular, infusion, via i.v. drip, patch and implant. In some embodiments the route of administration is intrapenile or directly onto the cavernosal tissue, connective tissue, or neurovascular structures of the penis. Additionally, the agents covered in this application can be applied intra-operatively or concomitantly with surgery to the site of surgery or remotely In accordance with some embodiments, it was found that that penile injection of SDF-1 also promotes healthy penile architecture including an increase in smooth muscle actin (SMA, smooth muscle fibers responsible for relaxation)), decreased in collagen scaring, and improved VEGF expression and protein expression (including improved vascularization of penile tissues, which is needed to deliver blood for penile engorgement and subsequent erection). Therefore, the methods of treatment described herein can be used to improve erectile function, by both improving and/or preserving functional penile architecture (which includes vasculature and nerves), as well as promoting nerve growth, and improved erectile and sexual function.

In one or more embodiments, the present invention provides pharmaceutical compositions comprising one or more of the inventive peptides and a pharmaceutically acceptable carrier. In other aspects, the pharmaceutical compositions also include one or more additional biologically active agents.

With respect to peptide compositions described herein, the carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use. Examples of the carriers include soluble carriers such as known buffers which can be physiologically acceptable (e.g., phosphate buffer) as well as solid compositions such as solid-state carriers or latex beads.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, or suspensions. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

In addition, in an embodiment, the compositions comprising the inventive peptides or derivatives thereof, may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular peptide containing compositions, as well as by the particular method used to administer the composition. Accordingly, there are a variety of suitable formulations of the pharmaceutical compositions of the invention. More than one route can be used to administer the compositions of the present invention, and in certain instances, a particular route can provide a more immediate and more effective response than another route.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

In accordance with some embodiments, the SDF-1 peptides or functional fragments or homologs thereof can be administered in the form of a hydrogel.

By "hydrogel" is meant a water-swellable polymeric matrix that can absorb water to form elastic gels, wherein "matrices" are three-dimensional networks of macromolecules held together by covalent or noncovalent crosslinks. On placement in an aqueous environment, dry hydrogels swell by the acquisition of liquid therein to the extent allowed by the degree of cross-linking.

A biologically compatible polymer refers to a polymer which is functionalized to serve as a composition for creating an implant. The polymer is one that is a naturally occurring polymer or one that is not toxic to the host. The polymer can, e.g., contain at least an imide. The polymer may be a homopolymer where all monomers are the same or a hetereopolymer containing two or more kinds of monomers. The terms "biocompatible polymer," "biocompatible cross-linked polymer matrix" and "biocompatibility" when used in relation to the instant polymers are art-recognized are considered equivalent to one another, including to biologically compatible polymer. For example, biocompatible polymers include polymers that are neither toxic to the host (e.g., an animal or human), nor degrade (if the polymer degrades at a rate that produces monomeric or oligomeric subunits or other byproducts at toxic concentrations in the host).

Polymer is used to refer to molecules composed of repeating monomer units, including homopolymers, block copolymers, heteropolymers, random copolymers, graft copolymers and so on. "Polymers" also include linear polymers as well as branched polymers, with branched polymers including highly branched, dendritic, and star polymers.

A monomer is the basic repeating unit in a polymer. A monomer may itself be a monomer or may be dimer or oligomer of at least two different monomers, and each dimer or oligomer is repeated in a polymer.

Biocompatible polymer, biocompatible cross-linked polymer matrix and biocompatibility are art-recognized. For example, biocompatible polymers include polymers that are neither themselves toxic to the host (e.g., and animal or human), nor degrade (if the polymer degrades) at a rate that produces monomeric or oligomeric subunits or other byproducts at toxic concentrations in the host. In certain embodiments of the present invention, biodegradation generally involves degradation of the polymer in an organism, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in certain embodiments, toxicology of a biodegradable polymer intended for in vivo use, such as implantation or injection into a patient, may be determined after one or more toxicity analyses. It is not necessary that any subject composition have a purity of 100% to be deemed biocompatible; indeed, it is only necessary that the subject compositions be biocompatible as set forth above. Hence, a subject composition may comprise polymers comprising 99%, 98%, 97%, 96%, 95%, 90%, 85%, 80%, 75% or even less of biocompatible polymers, e.g., including polymers and other materials and excipients described herein, and still be biocompatible.

To determine whether a polymer or other material is biocompatible, it may be necessary to conduct a toxicity analysis. Such assays are well known in the art, using, for example, chemical means or enzymatic means. An aliquot of the treated sample products are placed in culture plates previously seeded with the cells. The sample products are incubated with the cells. The results of the assay may be plotted as % relative growth vs. concentration of degraded sample.

In addition, monomers, polymers, polymer matrices, and formulations of the present invention may also be evaluated by well-known in vivo tests, such as subcutaneous implantations in rats to confirm that they do not cause significant levels of irritation or inflammation at the subcutaneous implantation sites.

"Biodegradable" is art-recognized, and includes monomers, polymers, polymer matrices, gels, compositions and formulations, such as those described herein, that are intended to degrade during use, such as in vivo. Biodegradable polymers and matrices typically differ from non-biodegradable polymers in that the former may be degraded during use. In certain embodiments, such use involves in vivo use, such as in vivo therapy, and in other certain embodiments, such use involves in vitro use. In general, degradation attributable to biodegradability involves the degradation of a biodegradable polymer into its component subunits, or digestion, e.g., by a biochemical process, of the polymer into smaller, non-polymeric subunits. In certain embodiments, two different types of biodegradation may generally be identified. For example, one type of biodegradation may involve cleavage of bonds (whether covalent or otherwise) in the polymer backbone. In such biodegradation, monomers and oligomers typically result, and even more typically, such biodegradation occurs by cleavage of a bond connecting one or more of subunits of a polymer. In contrast, another type of biodegradation may involve cleavage of a bond (whether covalent or otherwise) internal to a side chain or that connects a side chain, functional group and so on to the polymer backbone. For example, a therapeutic agent, biologically active agent, or other chemical moiety attached as a side chain to the polymer backbone may be released by biodegradation. In certain embodiments, one or the other or both general types of biodegradation may occur during use of a polymer. As used herein, the term "biodegradation" encompasses both general types of biodegradation.

The degradation rate of a biodegradable polymer often depends in part on a variety of factors, including the chemical identity of the linkage responsible for any degradation, the molecular weight, crystallinity, biostability, and degree of cross-linking of such polymer, the physical characteristics of the implant, shape and size, and the mode and location of administration. For example, the greater the molecular weight, the higher the degree of crystallinity, and/or the greater the biostability, the biodegradation of any biodegradable polymer is usually slower. The term "biodegradable" is intended to cover materials and processes also termed "bioerodible."

In certain embodiments, the biodegradation rate of such polymer may be characterized by the presence of enzymes, for example, a chondroitinase. In such circumstances, the biodegradation rate may depend on not only the chemical identity and physical characteristics of the polymer matrix, but also on the identity of any such enzyme.

In certain embodiments, polymeric formulations of the present invention biodegrade within a period that is acceptable in the desired application. In certain embodiments, such as in vivo therapy, such degradation occurs in a period usually less than about five years, one year, six months, three months, one month, fifteen days, five days, three days, or even one day on exposure to a physiological solution with a pH between 6 and 8 having a temperature of between about 25 and 37° C. In other embodiments, the polymer degrades in a period of between about one hour and several weeks, depending on the desired application. In some embodiments, the polymer or polymer matrix may include a detectable agent that is released on degradation.

Cross-linked herein refers to a composition containing intermolecular cross-links and optionally intramolecular cross-links, arising from, generally, the formation of covalent bonds. Covalent bonding between two cross-linkable components may be direct, in which case an atom in one component is directly bound to an atom in the other component, or it may be indirect, through a linking group. A cross-linked gel or polymer matrix may, in addition to covalent, also include intermolecular and/or intramolecular noncovalent bonds such as hydrogen bonds and electrostatic (ionic) bonds.

"Gel" refers to a state of matter between liquid and solid, and is generally defined as a cross-linked polymer network swollen in a liquid medium. Typically, a gel is a two-phase colloidal dispersion containing both solid and liquid, wherein the amount of solid is greater than that in the two-phase colloidal dispersion referred to as a "sol." As such, a "gel" has some of the properties of a liquid (i.e., the shape is resilient and deformable) and some of the properties of a solid (i.e., the shape is discrete enough to maintain three dimensions on a two-dimensional surface).

Hydrogels consist of hydrophilic polymers cross-linked to from a water-swollen, insoluble polymer network. Cross-linking can be initiated by many physical or chemical mechanisms. Photopolymerization is a method of covalently crosslink polymer chains, whereby a photoinitiator and polymer solution (termed "pre-gel" solution) are exposed to a light source specific to the photoinitiator. On activation, the photoinitiator reacts with specific functional groups in the polymer chains, crosslinking them to form the hydrogel. The reaction is rapid (3-5 minutes) and proceeds at room and body temperature. Photoinduced gelation enables spatial and temporal control of scaffold formation, permitting shape manipulation after injection and during gelation in vivo. Cells and bioactive factors can be easily incorporated into the hydrogel scaffold by simply mixing with the polymer solution prior to photogelation.

Alternatively, the reactants can contain complementary reactive groups, as an imide and an amide, that yield cross-linking without the need of an external initiator.

Hydrogels of interest can be semi-interpenetrating networks that promote cell, tissue and organ repair. The hydrogels of interest also are configured to have a viscosity that will enable the gelled hydrogel to remain affixed on or in the cell, tissue or organ, or surface. Viscosity can be controlled by the monomers and polymers used, by the level of water trapped in the hydrogel, and by incorporated thickeners, such as biopolymers, such as proteins, lipids, saccharides and the like. An example of such a thickener is hyaluronic acid or collagen.

"Incorporated," "encapsulated," and "entrapped" are art-recognized when used in reference to a therapeutic agent, dye, or other material and a polymeric composition, such as a composition of the present invention. In certain embodiments, these terms include incorporating, formulating or otherwise including such agent into a composition that allows for sustained release of such agent in the desired application. The terms may contemplate any manner by which a therapeutic agent or other material is incorporated into a polymer matrix, including, for example, attached to a monomer of such polymer (by covalent or other binding interaction) and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to the incorporation of a therapeutic agent or other material and at least one other therapeutic agent or other material in a subject composition.

More specifically, the physical form in which any therapeutic agent or other material is encapsulated in polymers may vary with the particular embodiment. For example, a therapeutic agent or other material may be first encapsulated in a microsphere and then combined with the polymer in such a way that at least a portion of the microsphere structure is maintained. Alternatively, a therapeutic agent or other material may be sufficiently immiscible in the polymer of the invention that it is dispersed as small droplets, rather than being dissolved in the polymer. Any form of encapsulation or incorporation is contemplated by the present invention, in so much as the sustained release of any encapsulated therapeutic agent or other material determines whether the form of encapsulation is sufficiently acceptable for any particular use.

Cross-linked polymer matrices of the present invention may include and form hydrogels. The water content of a hydrogel may provide information on the pore structure. Further, the water content may be a factor that influences, for example, the survival of encapsulated cells within the hydrogel. The amount of water that a hydrogel is able to absorb may be related to the cross-linking density and/or pore size. For example, the percentage of imides on a functionalized macromer, such as chondroitin sulfate, hyaluronic acid, dextran, carboxy methyl starch, keratin sulfate, or ethyl cellulose, may dictate the amount of water that is absorbable.

The compositions of the present invention may comprise monomers, macromers, oligomers, polymers, or a mixture thereof. The polymer compositions can consist solely of covalently crosslinkable polymers, or ionically crosslinkable polymers, or polymers crosslinkable by redox chemistry, or polymers crosslinked by hydrogen bonding, or any combination thereof. The reagents should be substantially hydrophilic and biocompatible.

Suitable hydrophilic polymers include synthetic polymers such as poly(ethylene glycol), poly(ethylene oxide), partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll™, polysucrose, hyaluronic acid, dextran, heparan sulfate, chondroitin sulfate, heparin, or alginate, and proteins such as gelatin, collagen, albumin, or ovalbumin, carboxy methyl starch, or copolymers or blends thereof. As used herein, "celluloses" includes cellulose and derivatives of the types described above; "dextran" includes dextran and similar derivatives thereof.

Polysaccharides or other biologically compatible polymers that are very viscous liquids or that are thixotropic, and form a gel over time by the slow evolution of structure, are also useful. For example, hyaluronic acid, which can form an injectable gel with a consistency like a hair gel, may be utilized. Modified hyaluronic acid derivatives are particularly useful. As used herein, the term "modified hyaluronic acids" refers to chemically modified hyaluronic acids. Modified hyaluronic acids may be designed and synthesized with preselected chemical modifications to adjust the rate and degree of crosslinking and biodegradation. For example, modified hyaluronic acids may be designed and synthesized which are esterified with a relatively hydrophobic group such as propionic acid or benzylic acid to render the polymer more hydrophobic and gel-forming, or which are grafted with amines to promote electrostatic self-assembly. Modified hyaluronic acids thus may be synthesized which are injectable, in that they flow under stress, but maintain a gel-like structure when not under stress. Hyaluronic acid and hyaluronic derivatives are available from Genzyme Corp. (Cambridge, Mass.).

Methods for the synthesis of the polymers described above are known to those skilled in the art, see, e.g., Concise Encyclopedia of Polymer Science and Polymeric Amines and Ammonium Salts, E. Goethals, editor (Pergamen Press, Elmsford, N.Y. 1980). Many polymers, such as poly(acrylic acid), are commercially available. Naturally occurring polymers can be isolated from biological sources as known in the art or are commercially available. Naturally occurring and synthetic polymers may be modified using chemical reactions available in the art and described, for example, in March, "Advanced Organic Chemistry," 4th Edition, 1992, Wiley-Interscience Publication, New York.

Thus, in accordance with an embodiment, the present invention provides a method for treating or preventing erectile dysfunction of a subject by administering a composition comprising dendrimer nanoparticles intravenously or intrapenile; wherein the dendrimer nanoparticles comprise one or more ethylene diamine-core poly(amidoamine) (PAMAM) hydroxyl-terminated dendrimers covalently linked to at least one or SDF-1 peptides, or functional fragments or homologs thereof, in an amount effective for increasing neuronal growth in peripheral parasympathetic nervous tissue or increasing neuronal growth in major pelvic ganglions and cavernous nervous tissue in a subject.

As used herein, the term "PAMAM dendrimer" means poly(amidoamine) dendrimer, which may contain different cores, with amidoamine building blocks. The method for making them is known to those of skill in the art and generally, involves a two-step iterative reaction sequence that produces concentric shells (generations) of dendritic (3-alanine units around a central initiator core. This PAMAM core-shell architecture grows linearly in diameter as a function of added shells (generations). Meanwhile, the surface groups amplify exponentially at each generation according to dendritic-branching mathematics. They are available in generations G0—10 with 5 different core types and 10 functional surface groups. The dendrimer-branched polymer may consist of polyamidoamine (PAMAM), polyester, polyether, polylysine, or polyethylene glycol (PEG), polypeptide dendrimers.

In accordance with some embodiments, the PAMAM dendrimers used can be generation 4 dendrimers, with hydroxyl groups attached to their functional surface groups.

In some embodiments, the dendrimers are in nanoparticle form and are described in detail in international patent publication No. WO2009/046446, which is incorporated by reference herein.

As used herein, the term "nanoparticles", according to the definition from NNI (National Nanotechnology Initiative), are structures of sizes ranging from 1 to 100 nm in at least one dimension. However, the prefix "nano" is commonly used for particles that are up to several hundred nanometers in size. Nanocarriers with optimized physicochemical and biological properties are taken up by cells more easily than larger molecules, so they can be successfully used as delivery tools for currently available bioactive compounds. Liposomes, solid lipids nanoparticles, dendrimers, polymers, silicon or carbon materials, and magnetic nanoparticles are the examples of nanocarriers that have been tested as drug delivery systems.

The way of conjugating the drug to the nanocarrier and the strategy of its targeting is highly important for a targeted therapy. A drug may be adsorbed or covalently attached to the nanocarriers surface or else it can be encapsulated into it. Covalent linking has the advantage over other ways of attaching as it enables to control the number of drug molecules connected to the nanocarrier, i.e., a precise control of the amount of therapeutic compound delivered. Cell-specific targeting with nanocarriers may be accomplished by using active or passive mechanisms. The first strategy relies on the attraction of a drug—the nanocarriers conjugate to the affected site by using recognition ligands, attached to the surface of conjugates antibodies, low molecular ligands, e.g., folic acids, peptides, etc. The active strategy can be also achieved through a manipulation of physical stimuli (e.g., temperature, pH, magnetism).

As used herein, the term "incorporating" can include covalent linkage or electrostatic complexation of a biologically active agent, into the nanoparticle.

In accordance with some embodiments, the dendrimer nanoparticles comprise poly(amidoamine) (PAMAM) hydroxyl-terminated dendrimers incorporating at least one biologically active agent.

The nanoparticles used in the inventive methods may also include other dendritic polymers such as polyglycerols, polylysine, and polyester hyperbranched polymers. The drug can be incorporated into the dendrimers through covalent conjugation or electrostatic complexation. The nanoparticles may involve both biodegradable and non-biodegradable nanoparticles <50 nm in size.

In accordance with another embodiment, the dendrimer nanoparticles can comprise one or more polycationic polymers selected from the group consisting of linear or branched polycationic homopolymers, block polycationic copolymers and graft polycationic copolymers.

As used herein, the term "polycationic homopolymers" means polymer chains of repeating subunits that have cationic residues. Polycationic polymers are polymers that contain net positively charged atom(s) or associated group(s) of atoms covalently linked to the polymer molecules. This definition includes, but is not limited to phosphonium, sulfonium, and ammonium cations. Other examples of cationic groups that can be covalently linked include, but are not limited to, amines (primary, secondary, tertiary, and aromatic) isocyanates, polyacrylamides, polyisobutylene, poly(N-vinylcarbazole), and polyquatemium polymers.

Polycationic homopolymers useful in accordance with the present invention include, for example, polymers such as linear or branched homopolymers, including, for example, linear and/or branched polyethyleneimines and derivatives thereof, and polyphosphoroamidates and derivatives thereof.

In some embodiments, the dendrimer nanoparticles can comprise one or more polycationic polymers selected from the group consisting of linear or branched PEI, PPA, block polycationic copolymers comprising PEG and PEI or PPA and derivatives thereof, and graft polycationic copolymers comprising PEG and PEI or PPA and derivatives thereof.

As used herein, the term "derivatives" will be understood by those of ordinary skill in the art. Polycationic block and graft copolymers and their derivatives, can also be used in the nanoparticles, and include, for example, polyethylene glycol polymers. Examples of block copolymers useful in the present invention include, PEG-b-PPA, and derivatives thereof, and examples of polycationic graft copolymers useful in the present invention include, PEI-g-PEG and derivatives thereof.

Furthermore, it is understood that various embodiments comprising two or more different polycationic polymers can be used to produce the nanoparticles of the present invention.

As used herein, the polycationic polymers, including linear and branched polymers, as well as the block and graft copolymers used in various embodiments of the present invention, are derivatives of polycationic polymers that include biocompatible polymers (that is, polymers that do not cause significant undesired physiological reactions), that can be either biodegradable or non-biodegradable polymers or blends or copolymers thereof.

In accordance with some embodiments, the present invention provides a composition comprising one or more SDF-1, a functional fragment thereof); c) a functional homolog thereof) or functional fragment thereof and d) a fusion polypeptide comprising an amino acid sequence of any fragment and portion, and at least one or more biologically active agents.

As used herein the term "therapeutically active agent" or "biologically active agent" means an agent useful for the treatment or modulation of a disease or condition in a subject suffering therefrom. Examples of therapeutically active agents can include any drugs, peptides, siRNAs, and conjugates, known in the art for treatment of disease indications.

The biologically active agent may vary widely with the intended purpose for the composition. The term active is art-recognized and refers to any moiety that is a biologically, physiologically, or pharmacologically active substance that acts locally or systemically in a subject. Examples of biologically active agents, that may be referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment.

Further examples of biologically active agents include, without limitation, enzymes, receptor antagonists or agonists, hormones and antibodies. Specific examples of useful biologically active agents include, for example, autonomic agents, such as parasympathomimetics, cholinergic agonist parasympathomimetics, cholinesterase inhibitor parasympathomimetics, intravenous anesthetics, barbiturate intravenous anesthetics, benzodiazepine intravenous anesthetics, and opiate agonist intravenous anesthetics skeletal muscle relaxants, neuromuscular blocker skeletal muscle relaxants, and reverse neuromuscular blocker skeletal muscle relaxants.

In some embodiments, the examples of biologically active agents include, PDE-5 inhibitors, including sildenafil, tadalifil, vardenafil, avanafil, and other drugs such as alprostadil, for example.

In accordance with some embodiments, the SDF-1 peptides, functional fragments or functional homologs thereof can be administered using gene therapy approaches known in the art at the site of major pelvic ganglion or neurotrophic bundle of the subject.

Further provided by the invention is a nucleic acid comprising a nucleotide sequence encoding any of the SDF-1 polypeptides, or functional portions, homologs and functional variants thereof.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence which encodes any of the SDF-1 polypeptides, or functional portions or functional variants thereof. For example, the nucleic acid can comprise a nucleotide sequence comprising SEQ ID NOS: 1 or 2. The nucleotide sequence alternatively can comprise a nucleotide sequence which is degenerate to SEQ ID NOS: 1 or 2.

The invention also provides substituted nucleic acid sequences which encode any of the substituted SDF-1, polypeptides, homologs, or substituted functional portions or functional variants thereof.

In some embodiments, the substituted nucleic acid sequence may be optimized. Without being bound to a particular theory, it is believed that optimization of the nucleic acid sequence increases the translation efficiency of the mRNA transcripts. Optimization of the nucleic acid sequence may involve substituting a native codon for another codon that encodes the same amino acid, but can be translated by tRNA that is more readily available within a cell, thus increasing translation efficiency. Optimization of the nucleic acid sequence may also reduce secondary mRNA structures that would interfere with translation, thus increasing translation efficiency.

The invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions can be rendered more stringent by the addition of increasing amounts of formamide.

The nucleic acids of the invention can be incorporated into a recombinant expression vector.

Therefore, in accordance with some embodiments, the present methods can utilize a composition comprising a vector comprising a nucleic acid sequence encoding a) SDF-1; b) a functional fragment of a); c) a functional homolog of a) or b) or functional fragment thereof; and d) a fusion polypeptide comprising an amino acid sequence of any of a) to c).

In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes. In some embodiments, the marker gene can be luciferase or other photon emitting or fluorescent genes that enables the expression of the gene to be localized via imaging.

The recombinant expression vector can comprise a native or nonnative promoter operably linked to the nucleotide sequence encoding the SDF-1 polypeptide, or functional portions and functional variants thereof, or to the nucleotide sequence which is complementary to or which hybridizes to the nucleotide sequence encoding the SDF-1 polypeptide. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

The invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α $E.$ $coli$ cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant SDF-1, polypeptide, the host cell is preferably a mammalian cell. Most preferably, the host cell is a human cell.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect.

As used herein, the term "treat," as well as words stemming therefrom, includes diagnostic and preventative as well as disorder remitative treatment.

The dose of the compositions of the present invention also will be determined by the existence, nature and extent of any adverse side effects that might accompany the administration of a particular composition. Typically, an attending physician will decide the dosage of the pharmaceutical composition with which to treat each individual subject, taking into consideration a variety of factors, such as age, body weight, general health, diet, sex, compound to be administered, route of administration, and the severity of the condition being treated. By way of example, and not intending to limit the invention, the dose of the pharmaceutical compositions of the present invention can be about 0.001 to about 1000 mg/kg body weight of the subject being treated, from about 0.01 to about 100 mg/kg body weight, from about 0.1 mg/kg to about 10 mg/kg, and from about 0.5 mg to about 5 mg/kg body weight. In another embodiment, the dose of the pharmaceutical compositions of the present invention can be at a concentration from about 1 nM to about 10,000 nM, preferably from about 10 nM to about 5,000 nM, more preferably from about 10 nM to about 1000 nM.

In an alternate embodiment, the amount of SDF-1 administered would be between about 1 μg/ml to about 500 μg/ml, including 2 μg/ml, to 20 μg/ml, 40 μg/ml, 60 μg/ml, 80 μg/ml, 100 μg/ml, 200 μg/ml, 300 μg/ml, and 400 μg/ml, for example.

In another embodiment, the term "administering" means that at least one or more pharmaceutical compositions of the present invention are introduced into a subject, preferably a subject receiving treatment for a disease, and the at least one or more compositions are allowed to come in contact with the one or more disease related cells or population of cells.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

EXAMPLES

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

All experiments were approved by the Johns Hopkins University School of Medicine Animal Care and Use Committee in accordance with the National Institutes of Health Guide for the Care and Use of Laboratory Animals. Male Sprague-Dawley rats (Charles River, Wilmington, Mass.) weighing 300-325 grams were used and housed in 12 h light/dark lighting cycle with free access to food and water.

CNI and sham surgeries.

Under anesthesia, the prostate was exposed via a midline laparotomy and CN identified. CNI was induced by applying forceps for 15 seconds×3 to the nerve 2-3 mm distal to the MPG. In sham animals the CN were identified and the abdomen closed.

Quantitative PCR (qPCR).

MPGs from sham, 48 hour, 7, 14, 21, 30, 60 day rats were homogenized and total RNA was extracted and purified using the RNeasy system (Qiagen, Hilden, Germany), quantified and then reverse transcribed (GE Healthcore, Pittsburgh, Pa., USA). Real-time qPCR was performed using the StepOnePlus system (Applied Biosystems, Foster City, Calif., USA). TaqMan gene expression assays for VEGF, SMA, nNOS, SDF1, CXCR4, CXCR7 NGF, BDNF, GDNF and TH.

Example 1

Current model of erectile dysfunction is bilateral nerve crush injury model (BNCI) in rats. A schematic of the surgical model for ED is shown on FIG. 2.

Example 2

Penile Injections with rhSDF-1 Protein Facilitates Preservation of Erectile Function Following BCNI.

As shown in FIG. 2, intrapenile and/or intracavernosal injections with SDF-1 (concentration/vehicle 1 μg in 50 μl saline was injected once every other day for a total of 5 doses starting the day of cavernous nerve injury (BCNI). Intracavernosal pressure (ICP) was measured 14 days after injury allowing sufficient washout of SDF-1. Erectile function was improved in SDF-1 treated rats when compared to controls, and brought to levels close to sham control levels.

Figure 3A:
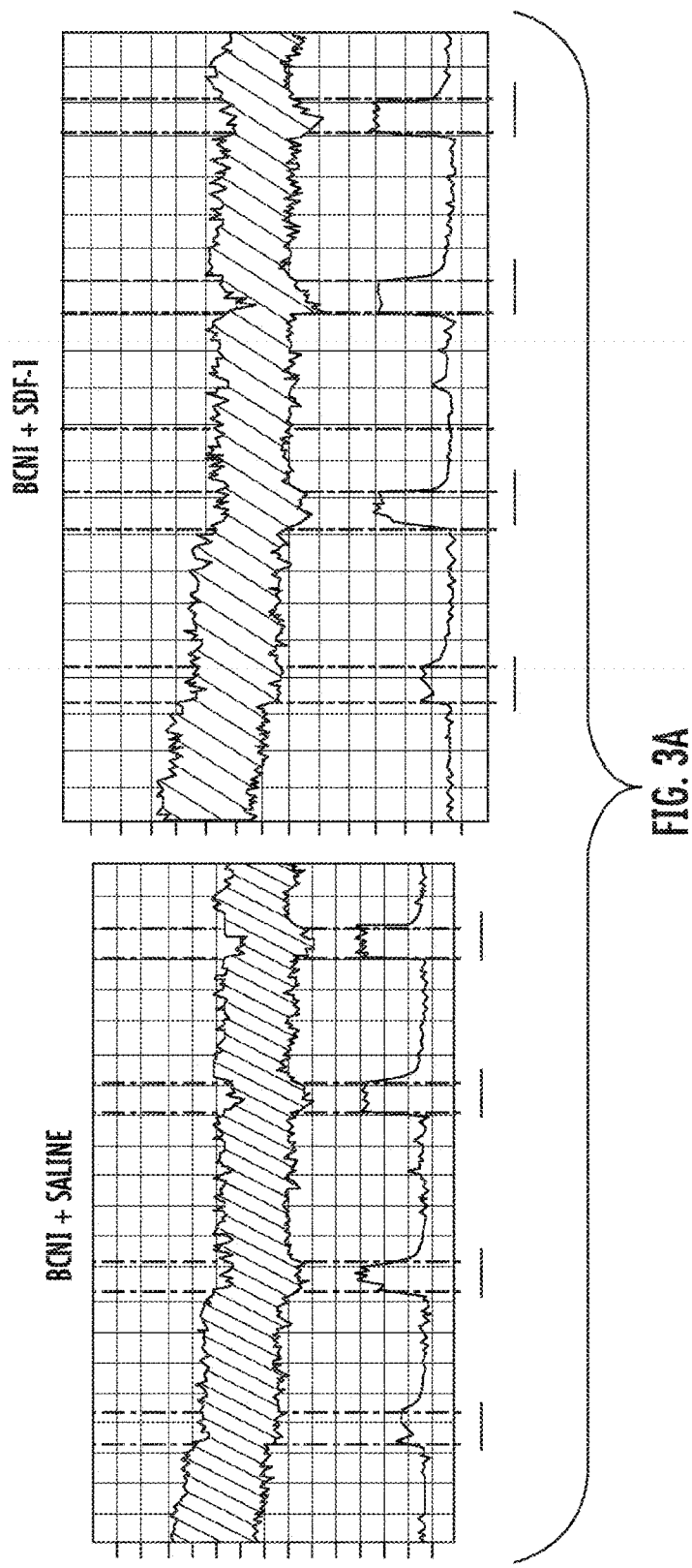
FIG. 3A shows ICP myograms with control rats with BCNI and those with BCNI and treated with 50 μg SDF-1 at site of injury.
Figure 3B:
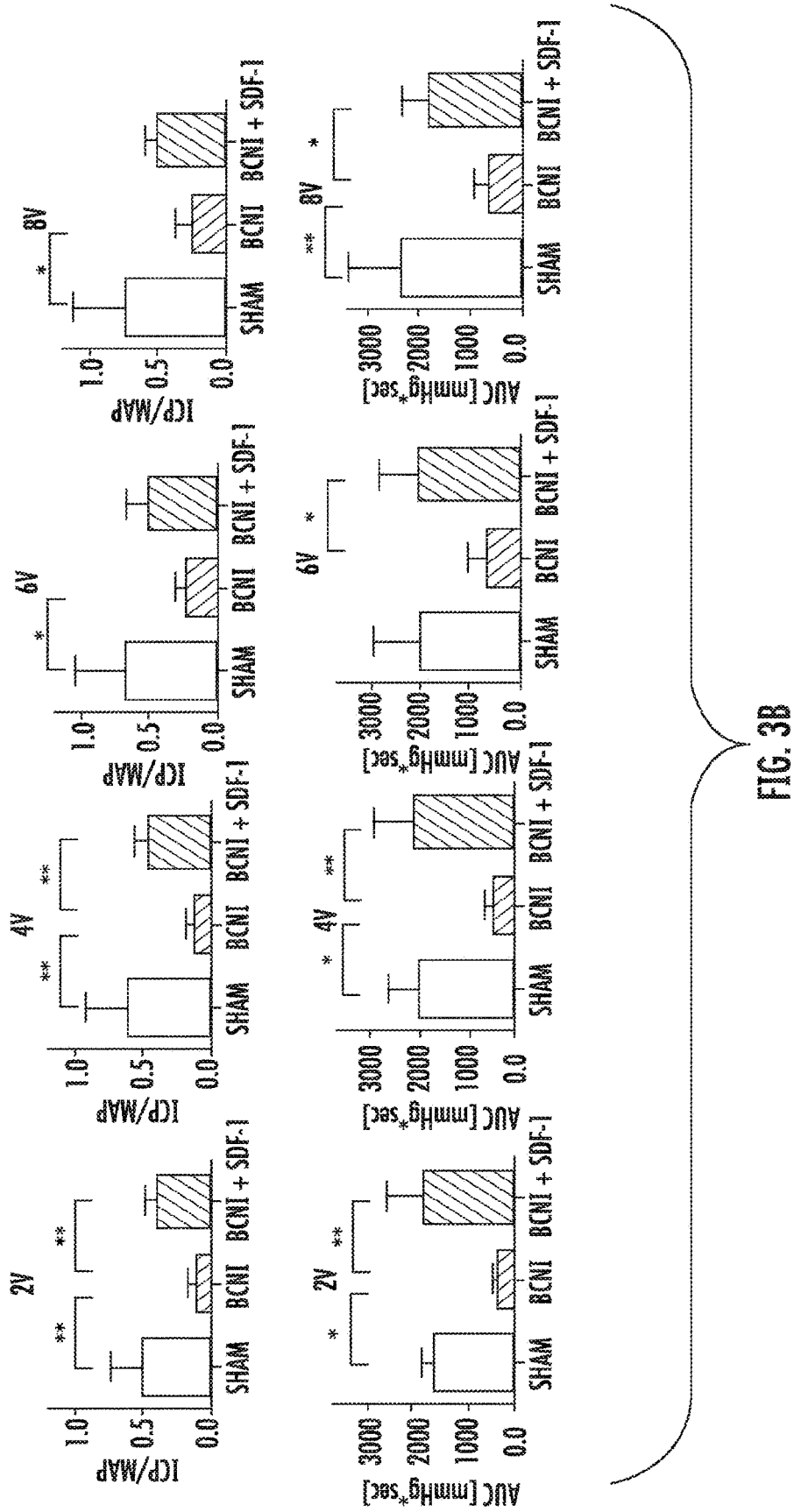
FIG. 3B shows summary graphs of ICP values for sham, BCNI alone and BCNI+SDF-1 treatment at a range of voltages from 2 volts to 8 volts (n=6 animals/group).

Under anesthesia, the prostate was exposed via a midline laparotomy and CN identified. CNI was induced by applying forceps for 15 seconds×3 to the nerve 2-3 mm distal to the MPG. In sham animals the CN were identified and the abdomen closed. Under anesthesia, the left crus was cannulated with a 25 G needle connected to a pressure transducer to measure intracavernous pressure (ICP). The right carotid artery was cannulated for continuous measurement of mean arterial pressure (MAP) (FIG. 3A). The CN distal to the crush injury was stimulated with a square pulse stimulator (Grass Instruments, Quincy, Mass., USA) at a frequency of 20 Hz, 0.5 msec duration, and a pulse width of 30 seconds, at a range between 2 volts and 8 volts for one minute. Outcome parameters used were ICP/MAP, peak ICP, and total ICP (area under the curve, AUC) (FIG. 3B) n=6/group.

Example 3

Penile Injections with rhSDF-1 greatly increases SDF1/CXCR4 axis expression and promotes beneficial penile morphology following BCNI.

Figure 4:
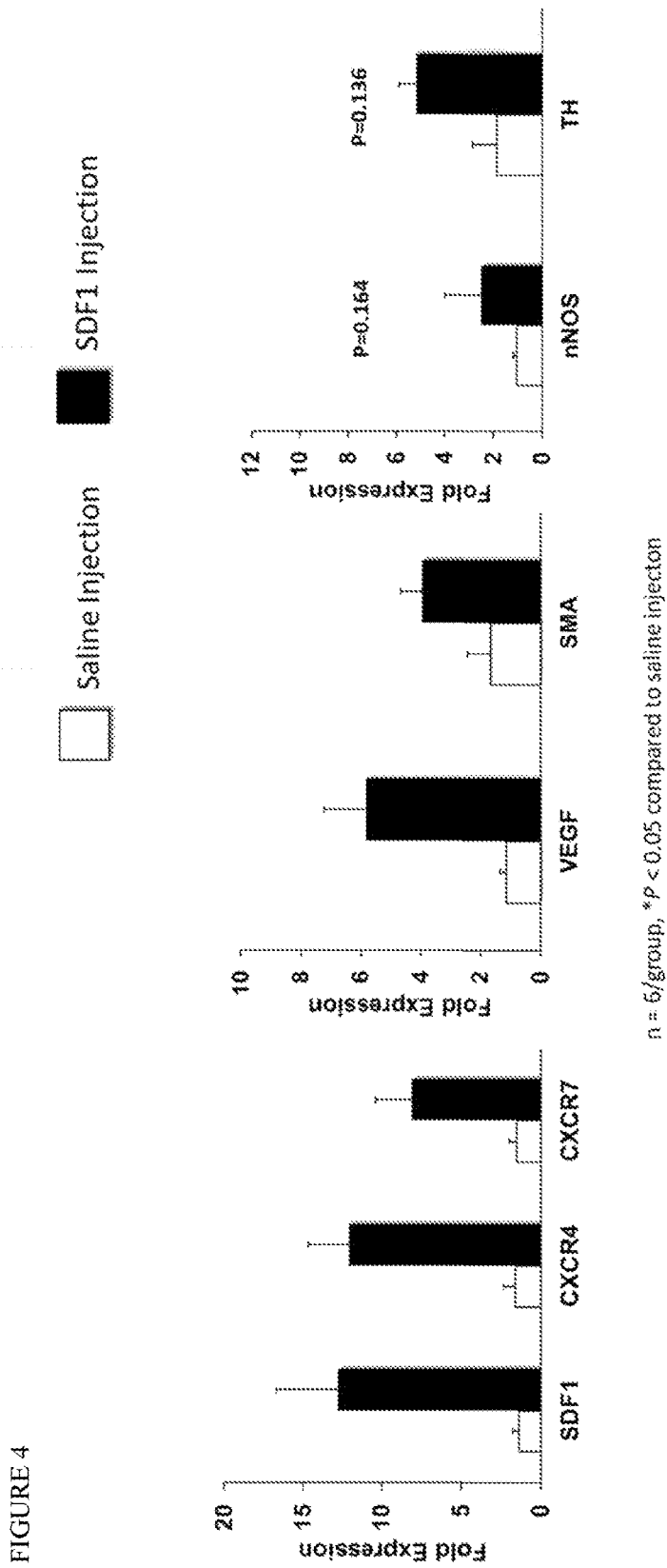
FIG. 4 shows that penile injections of rhSDF-1 increases penile tissue mRNA expression of SDF-1, CXCR4, CXCR7, VEGF and SMA after BCNI treatment when compared to saline controls. Graphs are fold expression over baseline.

In addition to ICP, molecular markers for neuronal growth through interaction of SDF-1 with its receptor CXCR4. As shown in FIG. 2, intrapenile injections with SDF-1 (concentration/vehicle 1 μg in 50 μl saline) was injected once every other day for a total of 5 doses starting the day of cavernous nerve injury (BCNI). Intracavernosal pressure (ICP) was measured 14 days after injury allowing sufficient washout of SDF-1. MPG and penile tissues were collected. mRNA expression of SDF-1, CXCR4, CXCR7, VEGF, smooth muscle actin (SMA), neural nitric oxide synthase (nNOS), and (TH) were measured in penile tissues. Levels of these markers were significantly increased over saline controls (n=6/group, *P<0.05 compared to saline injection). (FIG. 4).

Example 4

Figure 5A:
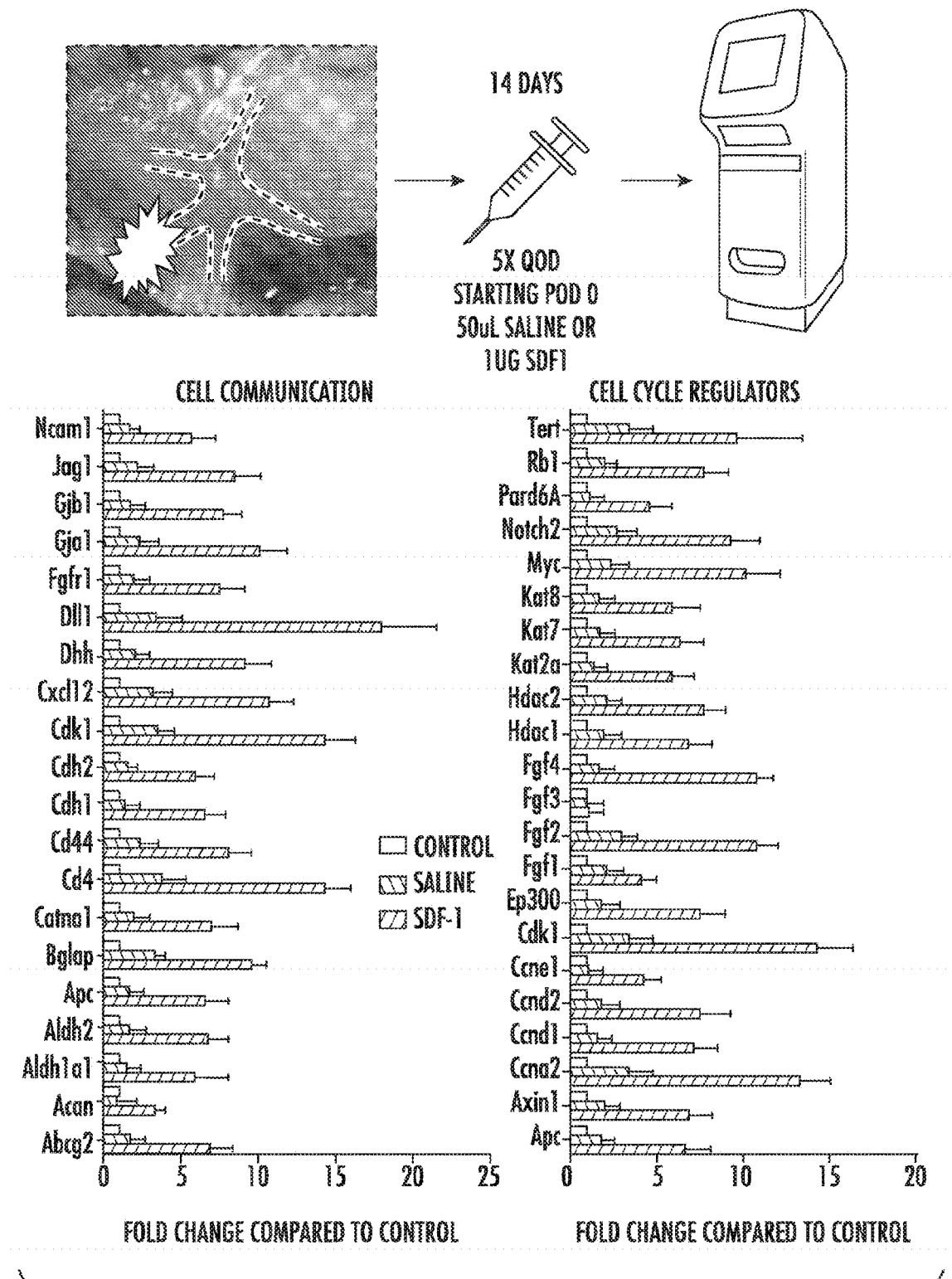
FIG. 5A shows a schematic diagram of the experimental procedure for penile injections of rhSDF-1 after BCNI. The bar graphs show increases gene expression in the major pelvic ganglion, which is remote from the site of injection, related to cell communication and cell cycle regulatory stem cell activity, when compared to controls.
Figure 5B:
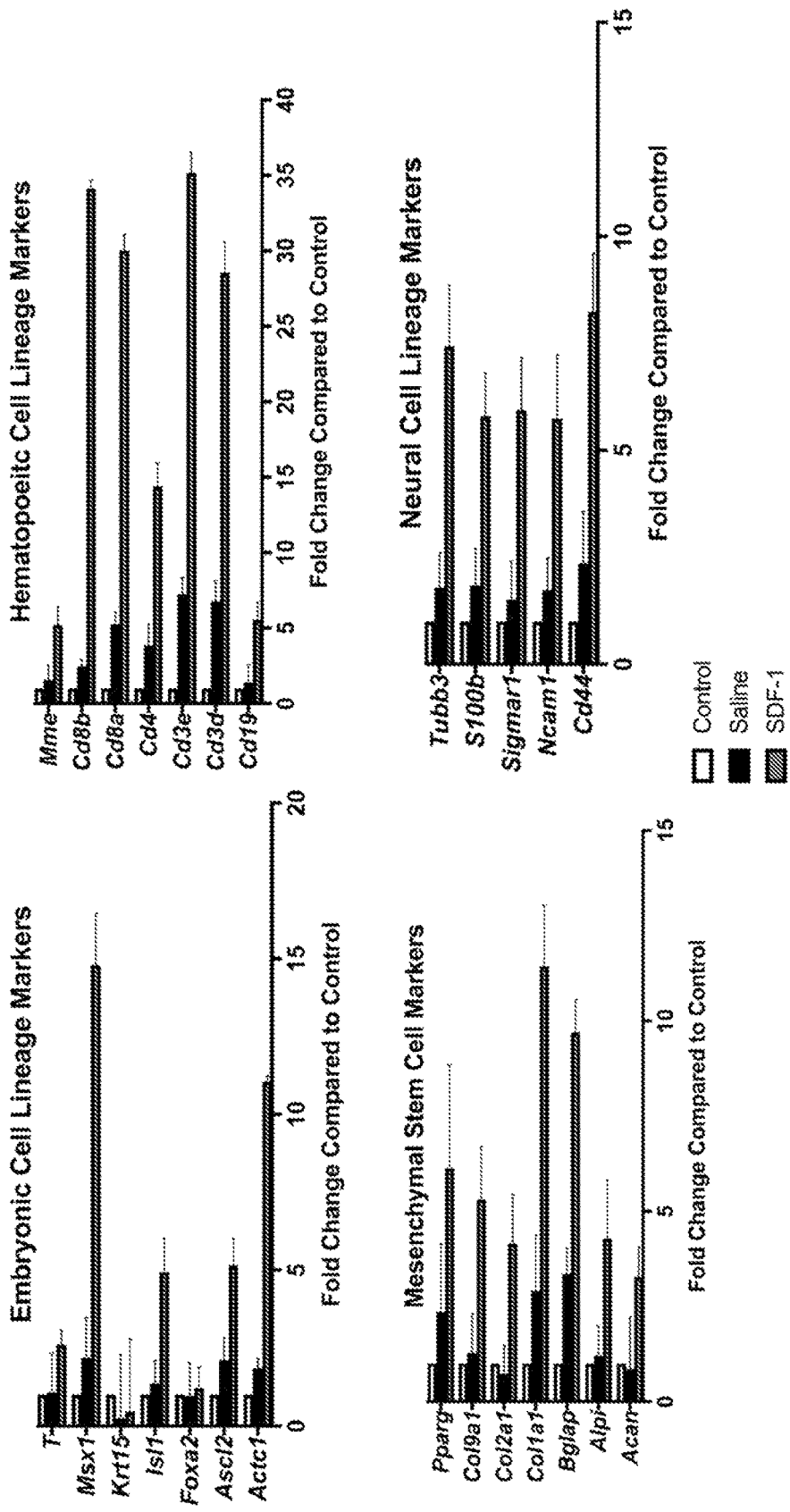
FIG. 5B are bar graphs showing increases gene expression markers for embryonic cell lineage markers, hematopoietic cell lineage markers, mesenchymal cell markers, and neural cell markers in the major pelvic ganglion after injection with SDF-1.
Figure 5C:
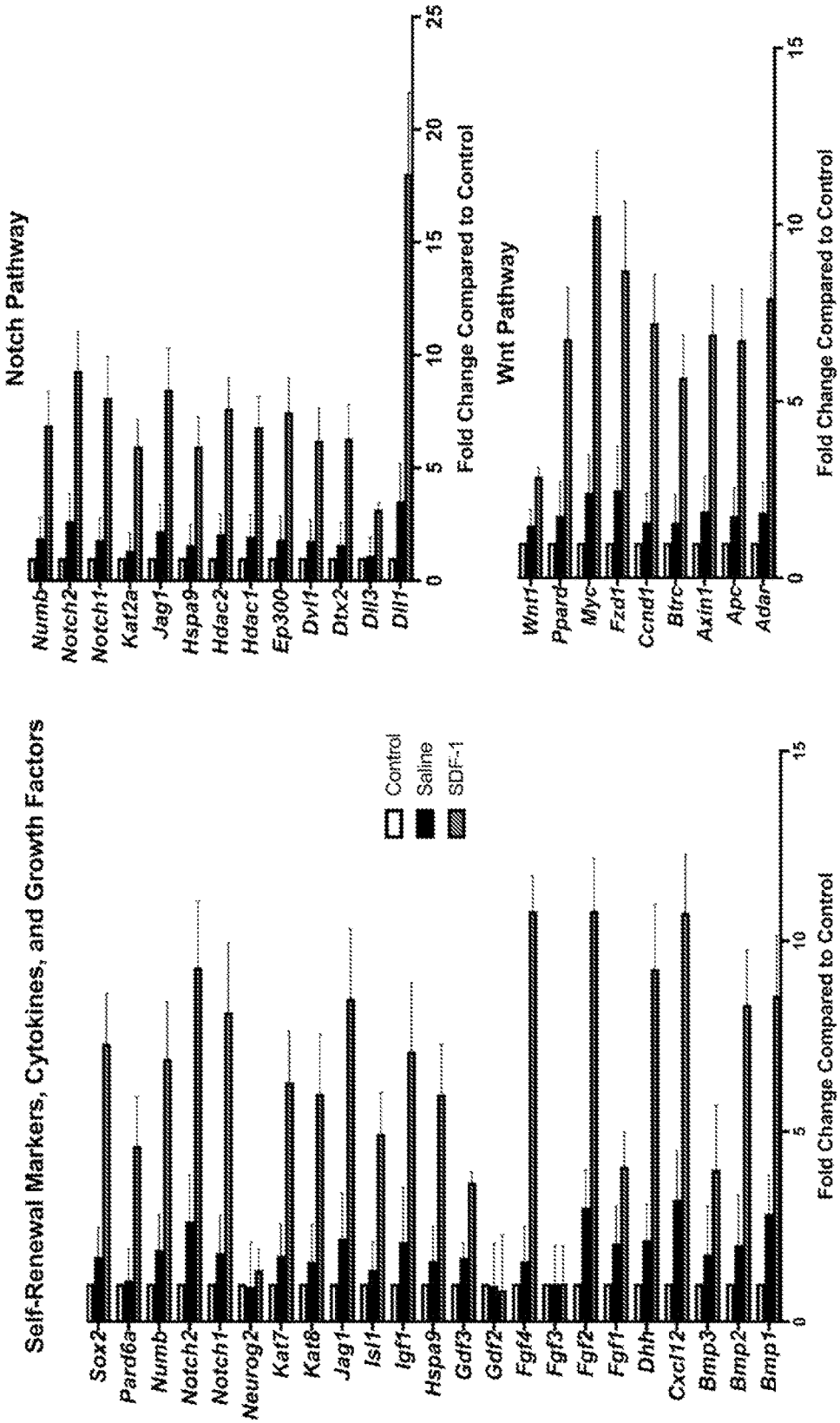
FIG. 5C are bar graphs showing increases gene expression markers for notch pathway markers, self-renewal, cytokines and growth factor markers, and Wnt pathway markers in the major pelvic ganglion after injection with SDF-1.
Figure 5D:
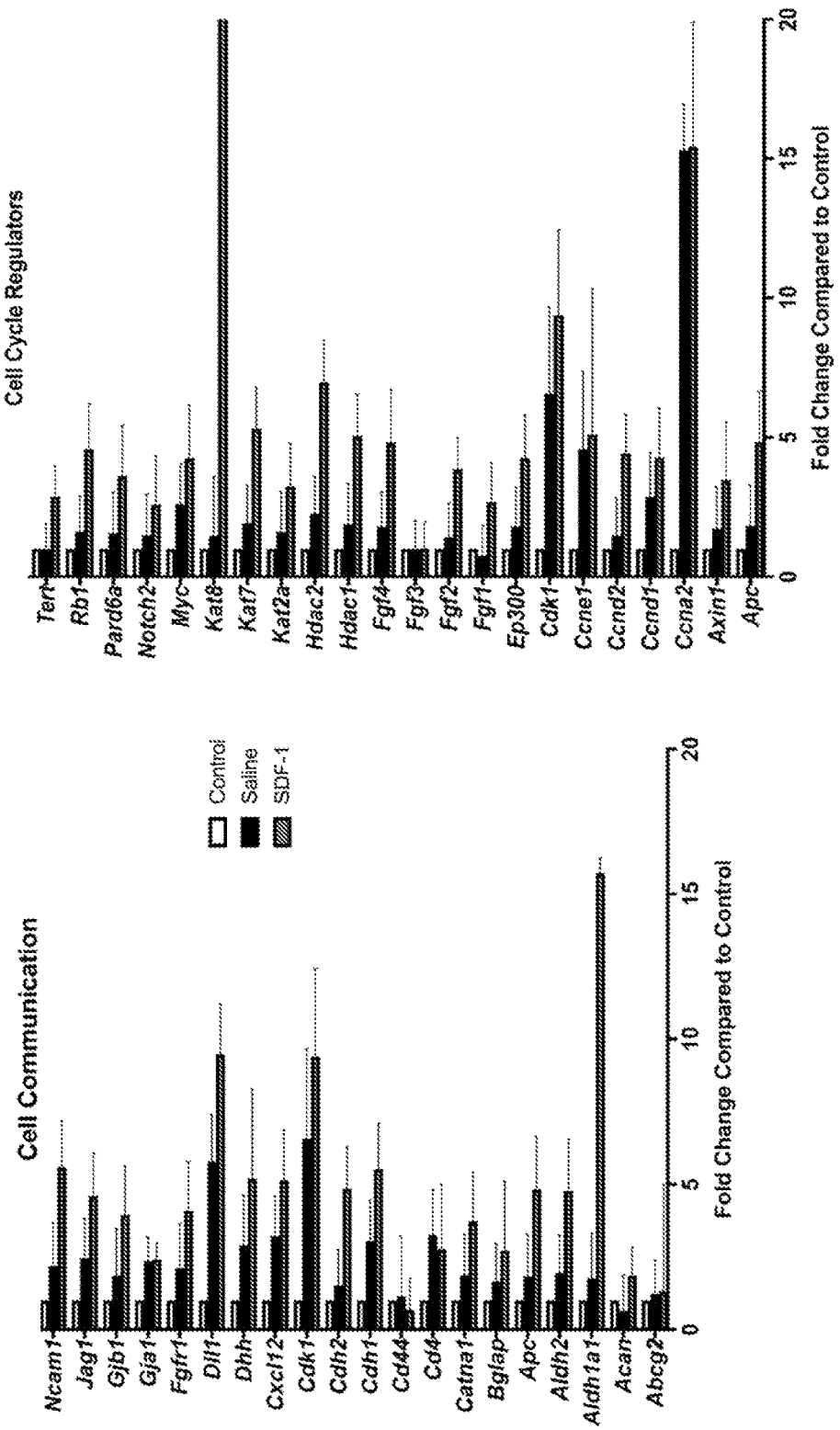
FIG. 5D are bar graphs showing increases gene expression markers in the penis for communication and cell cycle regulatory markers after injection with SDF-1.
Figure 5E:
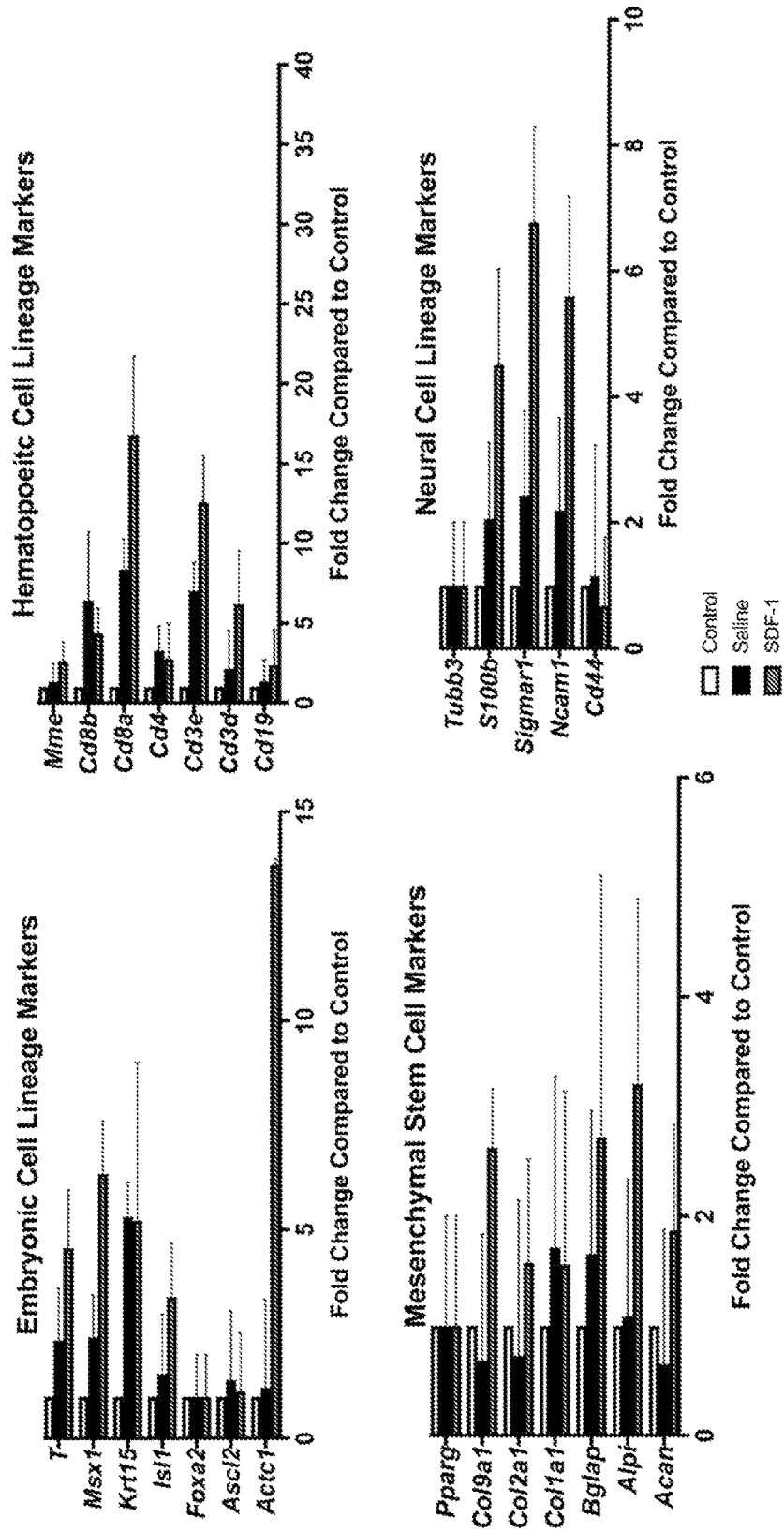
FIG. 5E are bar graphs showing increases gene expression markers for embryonic cell lineage markers, hematopoietic cell lineage markers, mesenchymal cell markers, and neural cell markers in the penis after injection with SDF-1.
Figure 5F:
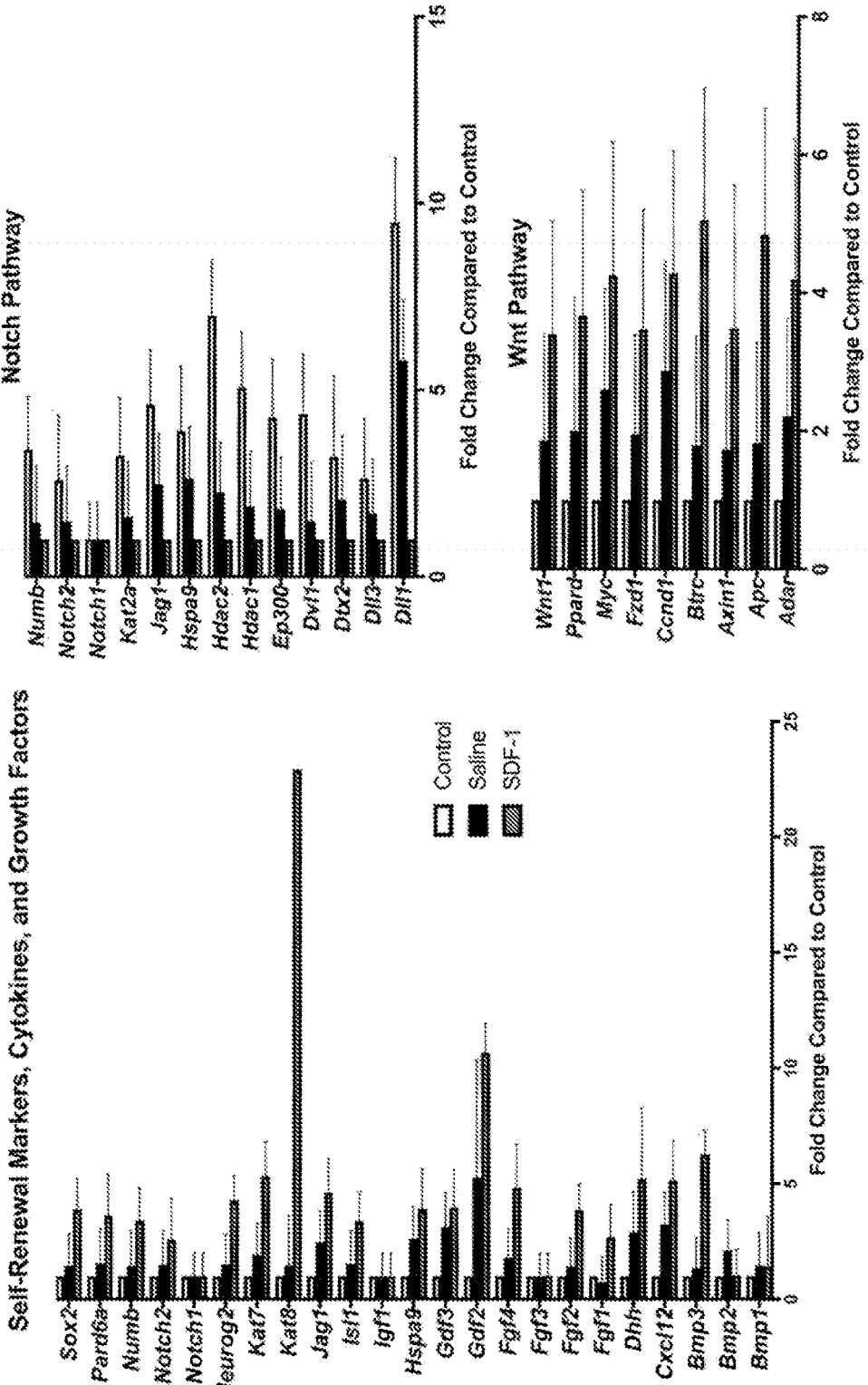
FIG. 5F are bar graphs showing increases gene expression markers for notch pathway markers, self-renewal, cytokines and growth factor markers, and Wnt pathway markers in the penis after injection with SDF-1.

Ex Vivo rat major pelvic ganglion cell culture. A schematic of the cell culture methods is shown in FIG. 5A.

Example 5 rhSDF-1 penile injections increases stem cell activity in the MPG following BCNI.
Using the same BCNI and treatment protocol as Example 2, major pelvic ganglion tissue from sham control, saline and SDF-1 treated rats were subjected to a genechip assay for identification of genes upregulated in the treated cases. The genes that were upregulated are shown on FIGS. 5A-5F.

Figure 6A:
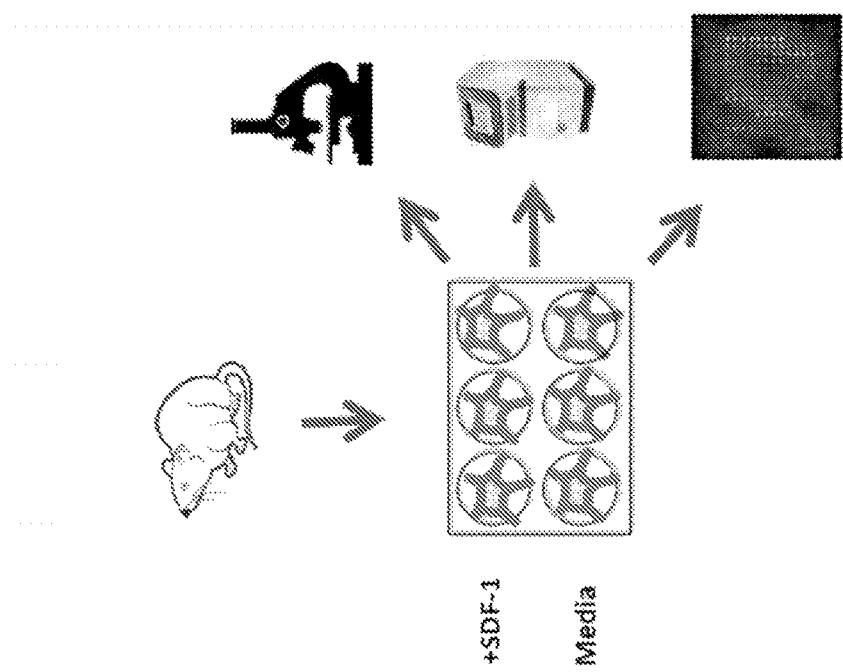
FIGS. 6A-6B are a schematic showing ex vivo primary cell culture of major pelvic ganglion neurons and treatment with SDF-1.
Figure 6A:
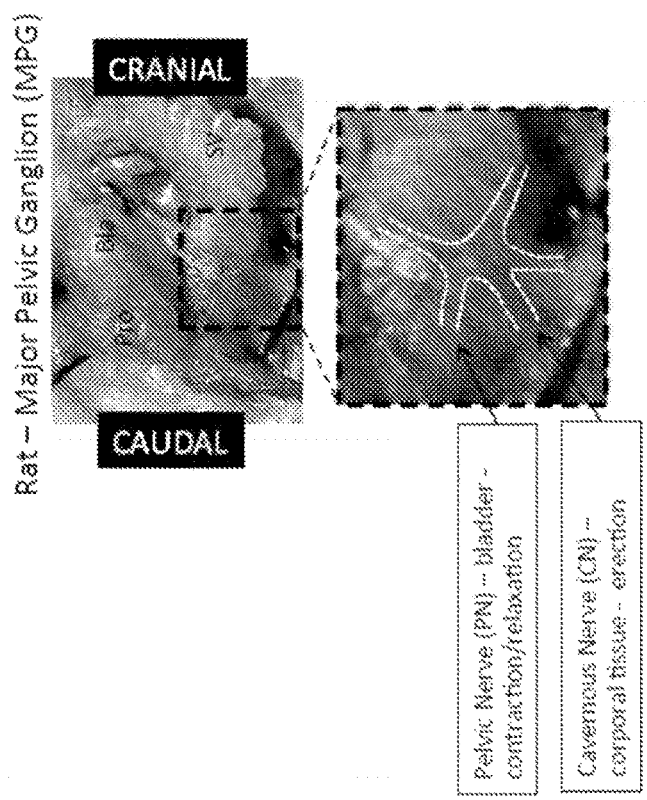
Figure 6B:
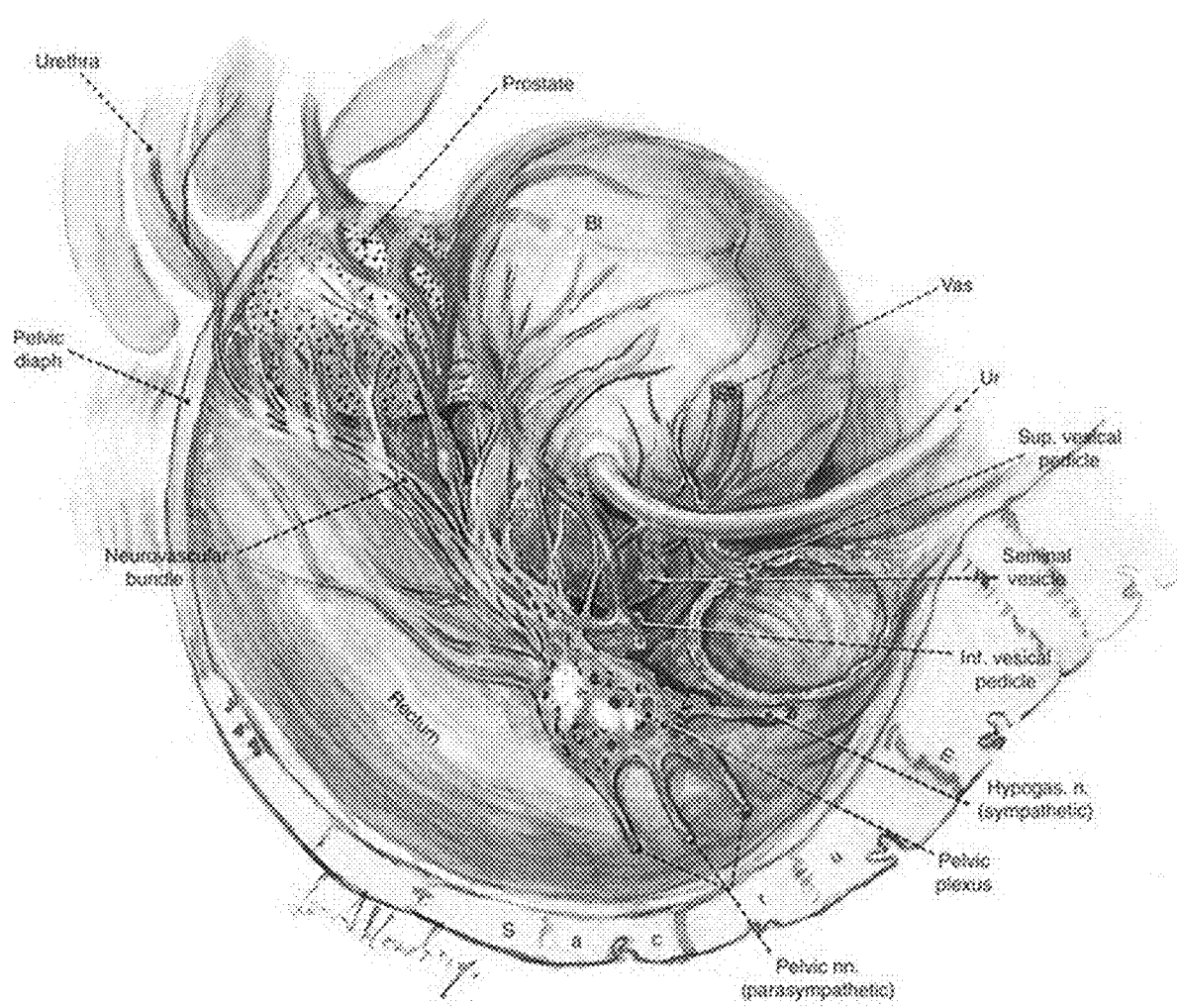
Figure 7:
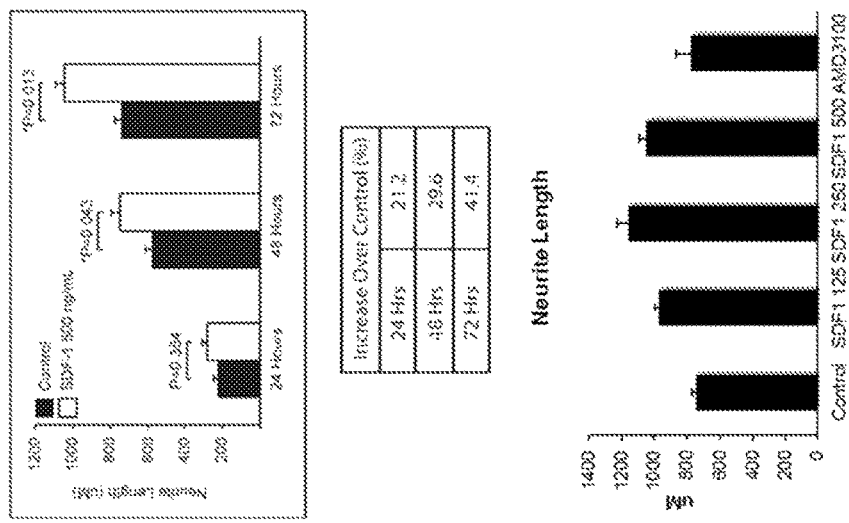
FIG. 7 depicts stimulation of neurite outgrowth on neurons from rat MPG in primary culture in the presence of SDF-1 from 24 to 72 hours.
Figure 7:
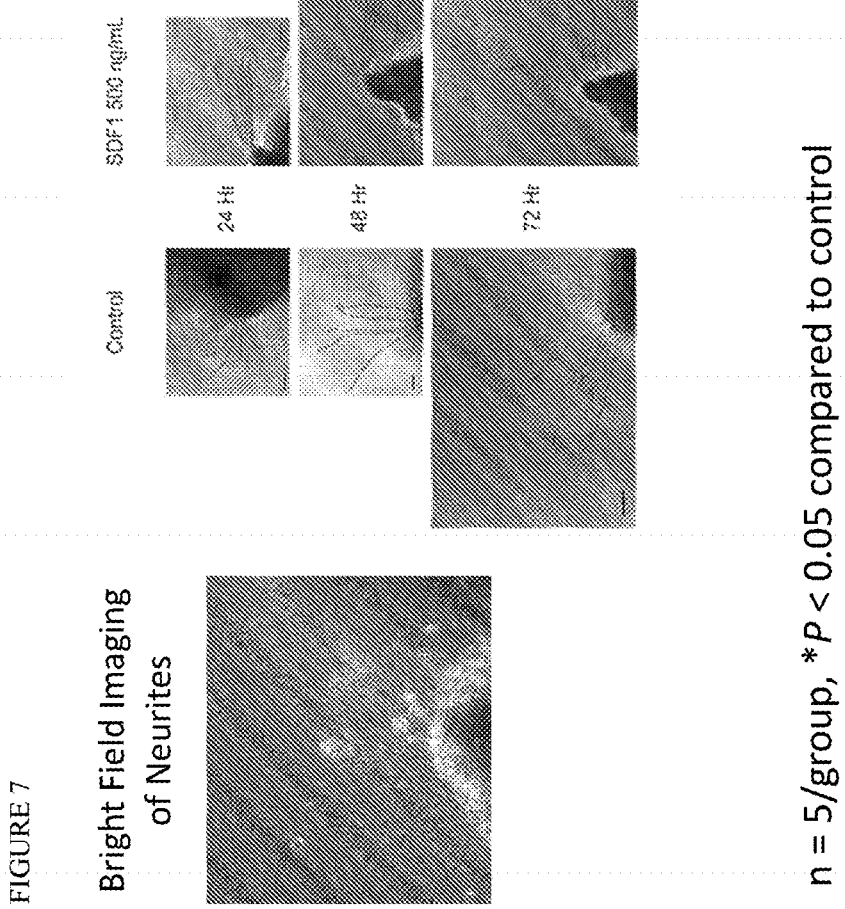

Example 6 rhSDF-1 protein facilitates neurite outgrowth from the MPGs cultured in matrigel for 72-hours via CXCR4 binding. Using the cell cultured MPG neurons described in Example 5 (FIG. 6), the neurons were exposed to saline or 500 ng/ml for 24, 48, or 72 hours and then neurite outgrowth was measured using brightfield imaging. SDF-1 showed increased neurite outgrowth over controls. The data show that 250 and 500 ng/ml SDF-1 were the concentrations that gave a significant increase. The antagonist, AMD-3100, lowered the SDF-1 to control levels (FIG. 7).

Figure 8:
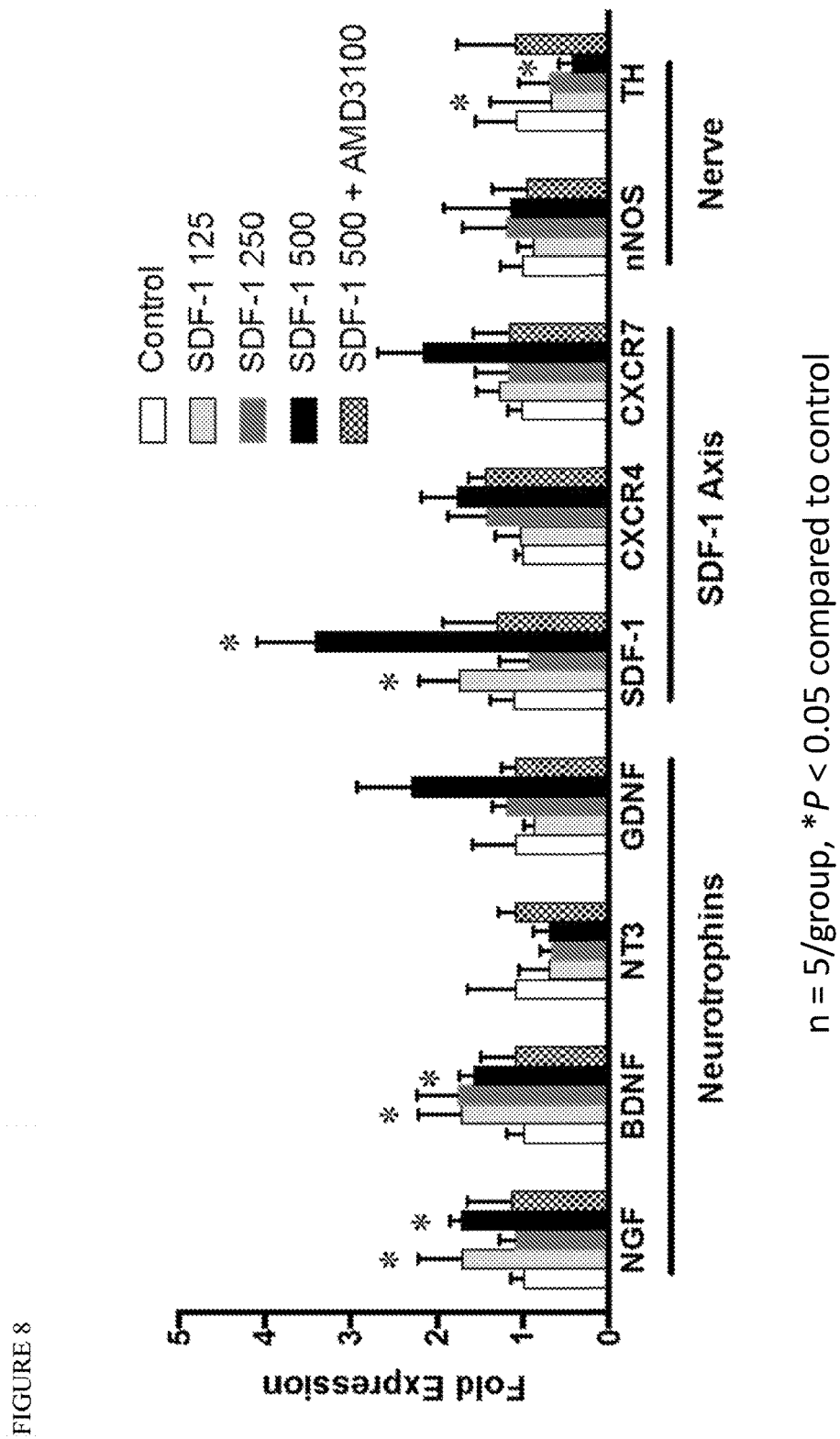
FIG. 8 shows graphs of gene expression in rat MPGs that were cultured in the presence of SDF-1 with an increase in mRNA expression of SDF-1 and neurotrophins and a decrease in tyrosine hydroxylase (TH) expression, which is a marker of inhibitory sympathetic neurons.

Example 7 rhSDF-1 treatment increases mRNA expression of neurotrophins and SDF-1, and decreases TH mRNA expression in cultured rat major pelvic ganglion neurons. Cell cultured MPG neurons were exposed to saline or 125, 500 ng/ml SDF-1, or AMD3100 in matrigel for 24, 48, and 72 hours and the cells were collected and mRNA extracted. Expression of NGF, BDNF, GDNF, SDF-1, were upregulated, and TH was decreased when compared to controls n=5/group, *P<0.05 compared to control (FIG. 8).

Figure 9:
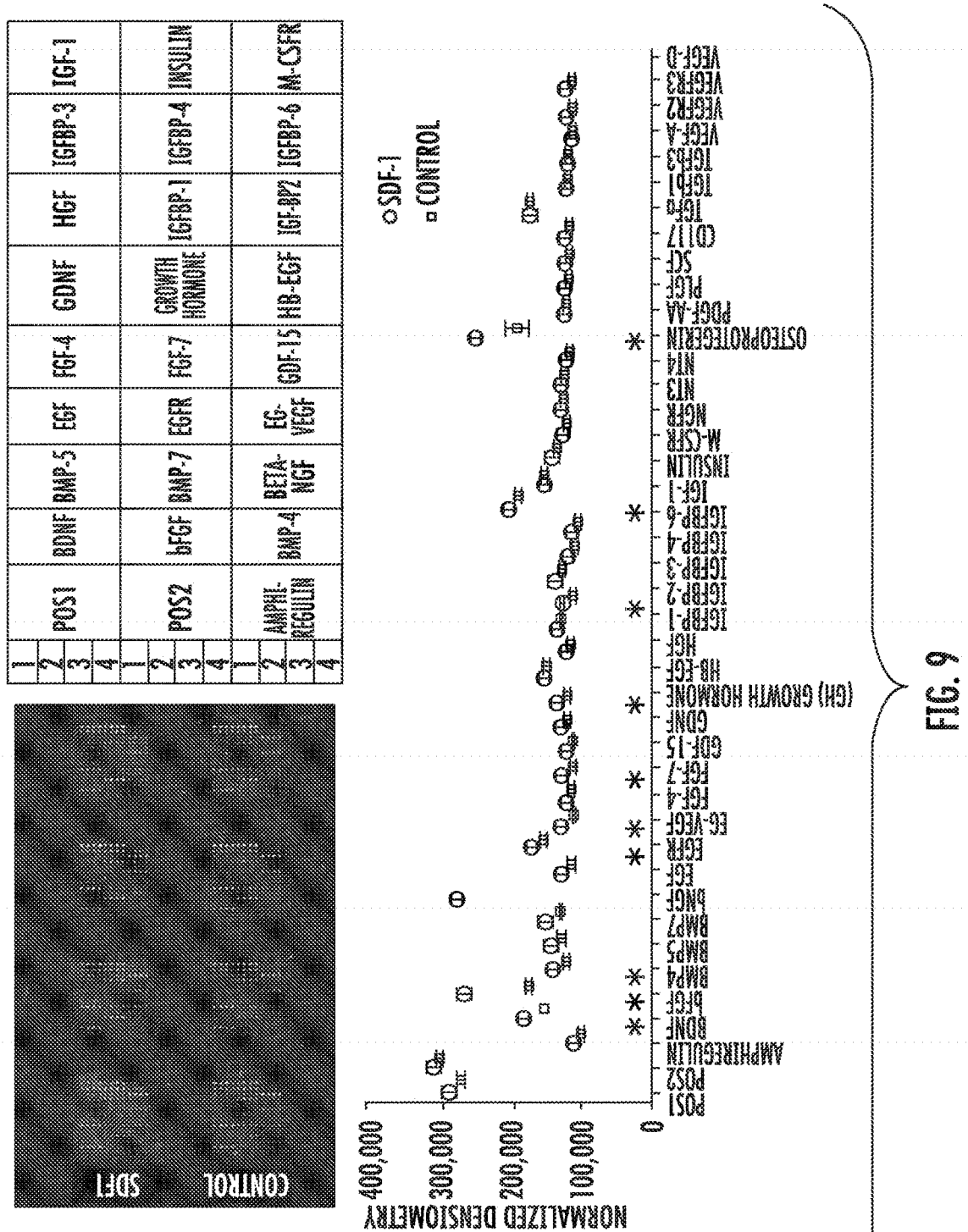
FIG. 9 depicts increased protein expression of certain growth factors in rat MPG in primary culture in the presence of SDF-1.

Example 8 rhSDF-1 Treatment Increases protein expression of growth factors in cultured MPGs. As shown in FIG. 9, expression of BDNF, bFGF, BMP4, EGFR, EG-VEGF, GH, IGFBP-2, and PDGβ-AA were upregulated when compared to controls.

Example 9

Figure 10:
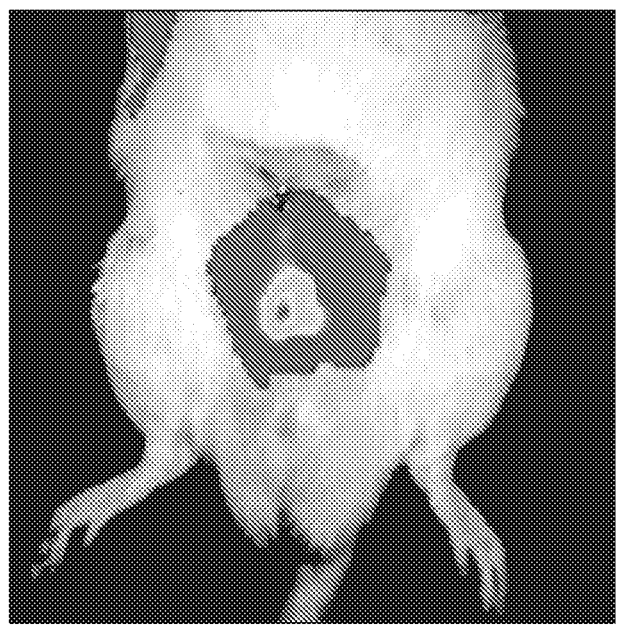
FIG. 10 shows luminescence from successful plasmid-based gene transfer targeting the major pelvic ganglion (left panel) and the penis (right panel).
Figure 10:
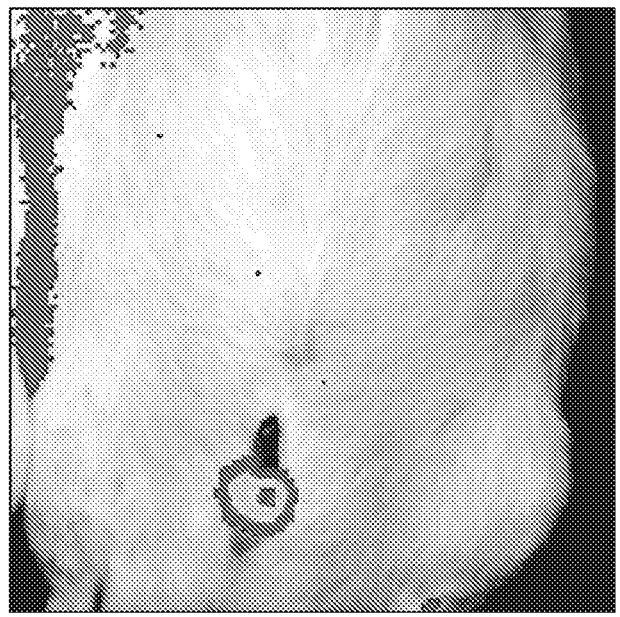

SDF-1 can be administered to the pelvic ganglion via gene therapy. SDF-1 was placed into a non-viral DNA vector and administered to rat pelvic ganglion with a luminescent reporter (FIG. 10).

Example 10

Short course of rhSDF-1 treatment does not affect prostate cancer tumor growth or disseminated tumor cell burden.
Nude mice with implanted prostate tumors located in the flank were treated with SDF-1 or saline controls, and tumors, body weight and penile weights were measured two and four weeks after injection. There was no significant difference in tumor growth or body or penile weight during the course of the experiment (FIG. 11) rhSDF-1 penile treatment did not increase tumor size, metastases, or disease progression in nude mice with aggressive prostate cancer tumors implanted into their flank.

Example 11

Figure 11:
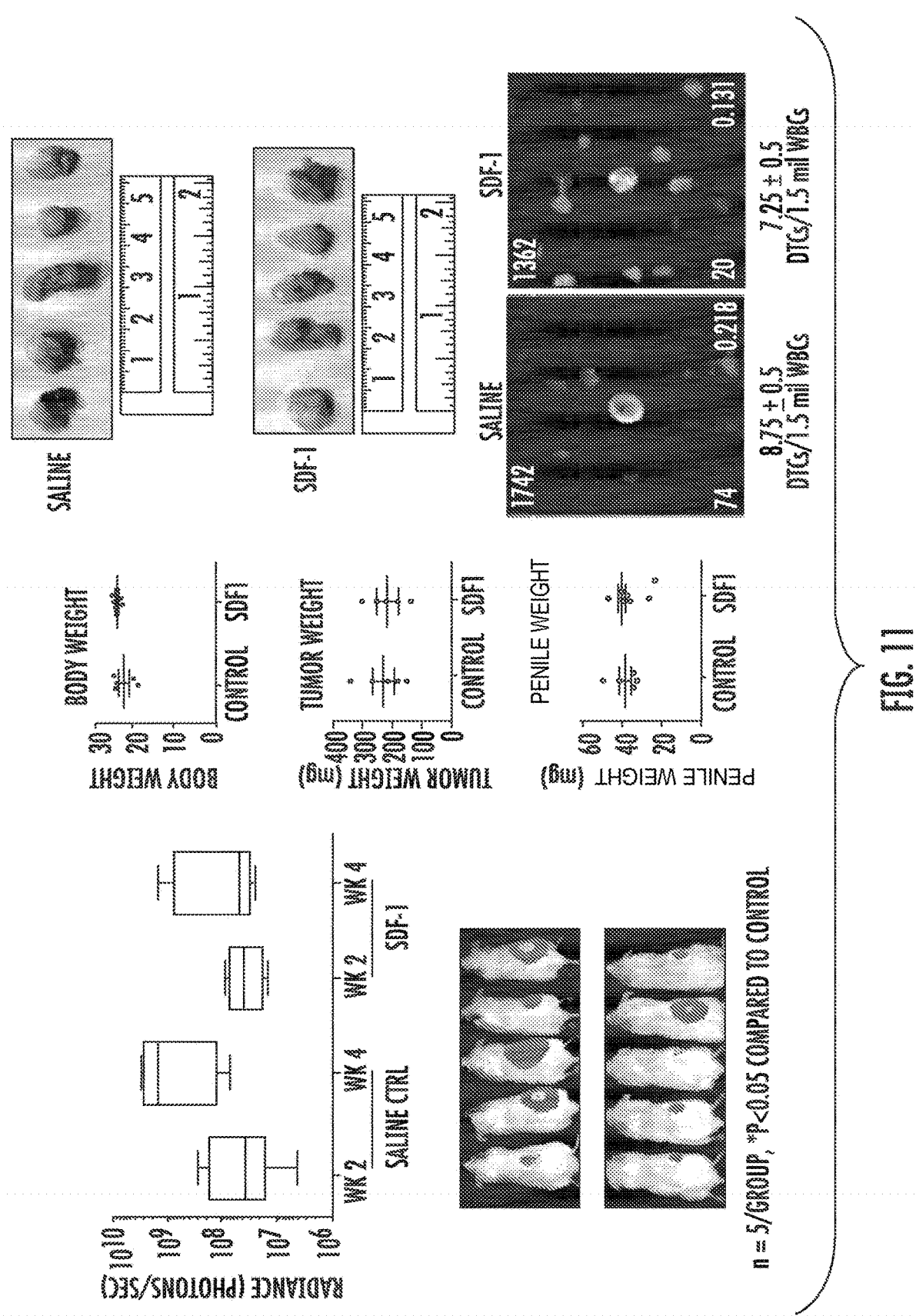
FIG. 11 shows that administration of rhSDF-1 into nude mice having prostate tumors implanted in their flank, did not significantly affect tumor growth, body weight or penile weight in the mice over 2 to 4 weeks' time.
Figure 12A:
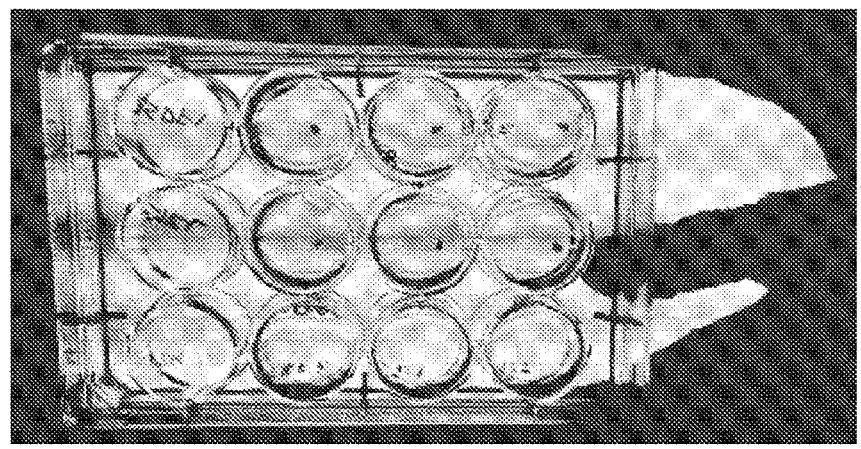
FIGS. 12A-12B depict experiments where MPGs from rats were cultured in vitro in hydrogels with SDF-1 or controls. Neurite outgrowths from the MPGs were measured.
Figure 12B:
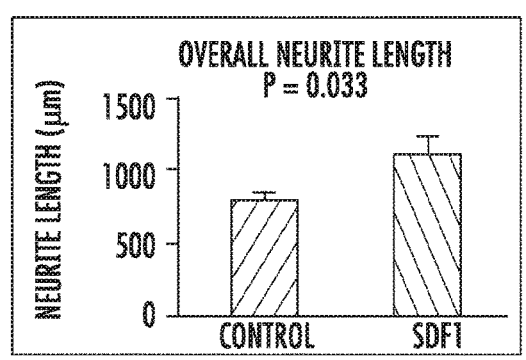
Figure 12B:
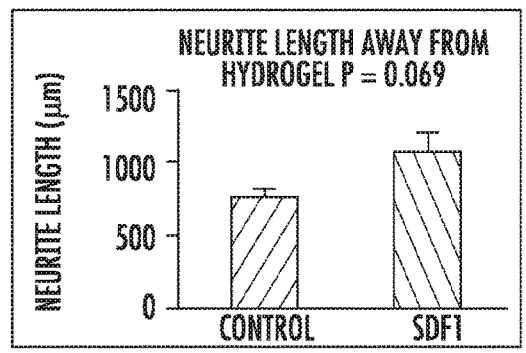
Figure 12B:
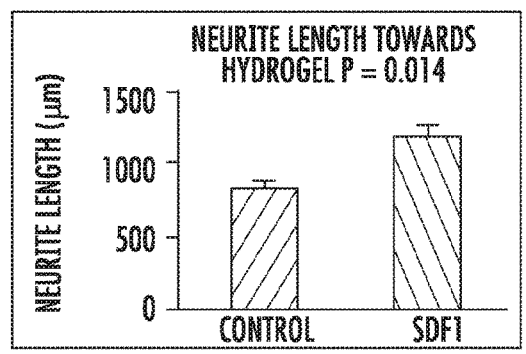
Figure 13A:
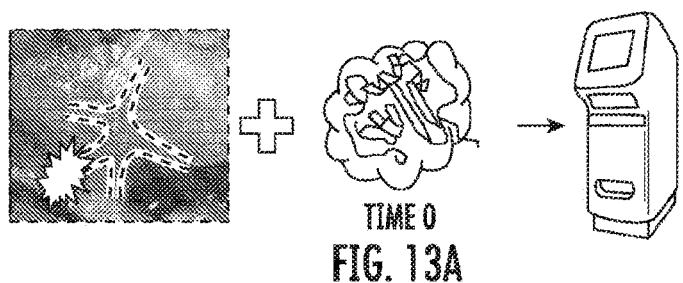
FIGS. 13A-13D depict in vivo experiments on rat MPGs where rats underwent BCNI and then were treated with either SDF-1 in a hydrogel formulation, or a hydrogel control solution was applied. A) A schematic diagram of the experimental protocol; B) is a photograph showing the rat MPG and a white outline of where the SDF-1 hydrogel was applied; C) is a graph showing mRNA expression of various markers of neuronal growth in treated MPG vs. controls; D) is a graph showing mRNA expression of neuronal growth factors in treated MPG vs. controls.
Figure 13B:
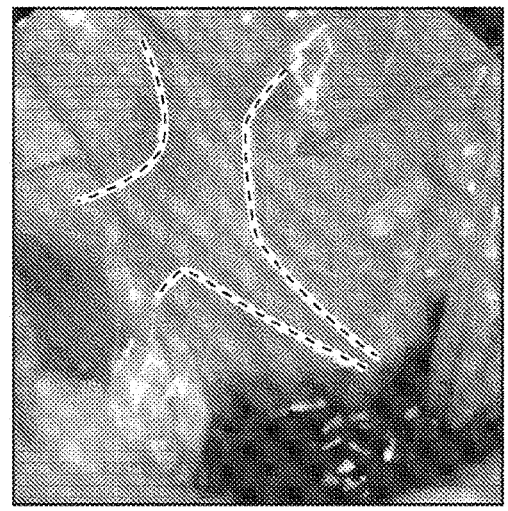
Figure 13C:
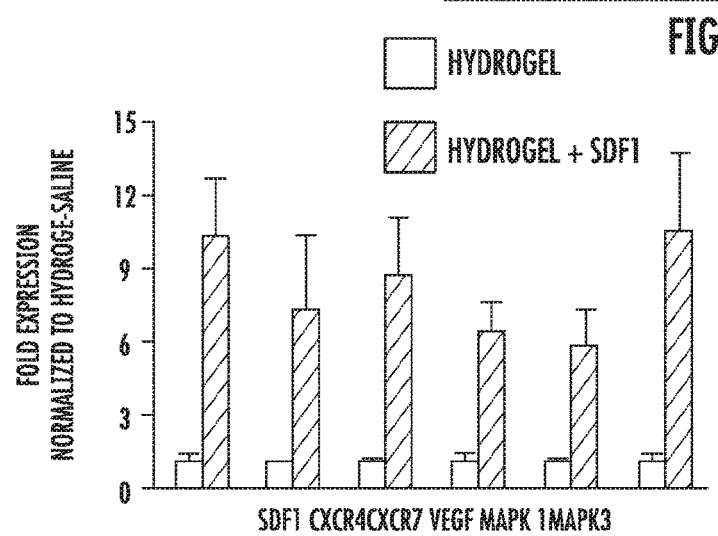
Figure 13D:
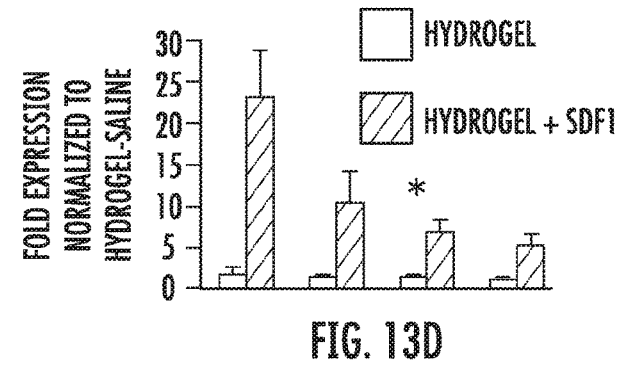

Hydrogel-based delivery of rhSDF1 to the Major Pelvic Ganglion.
Hydrogels or other biomaterials such has vicryl scaffolds etc. can be used to allowed a sustained, controlled, prolonged release of SDF-1 protein to a directed site including the neurovascular bundle placed at the time of prostatectomy or pelvic surgery, cavernous nerves during the time of penile surgery, or injected into the penis to treat existing erectile dysfunction (FIG. 11).
MPGs from rats were cultured ex-vivo for 3 days. They were either co-cultured with hydrogel with saline or hydrogel with rhSDF-1. Neurite outgrowth from the MPG were measured. As shown in FIGS. 12A-12B, there was a significant increase in overall neurite length in MPGs co-cultured with hydrogel rhSDF-1 compared to hydrogel-saline. There was a significant increase in neurites growing towards the hydrogel in MPGs co-cultured with hydrogel rhSDF-1.

Example 12

Rats underwent BCNI and hydrogel-SDF-1 or hydrogel-saline was placed over MPG in the rats. Penile tissue was collected 2-weeks later and qPCR was performed to measure gene expression of SDF-1 and other gene markers. The results showed that penile tissue from rats treated with hydrogel-SDF-1 had greater neurotropic, SDF-1-axis, survival, and angiogenic gene expression compared to rats treated with hydrogel-saline (FIGS. 13A-13D).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treating erectile dysfunction in a male subject in need thereof comprising administering to the major pelvic ganglion of the subject an effective amount of a composition comprising a polypeptide having the amino acid sequence set forth in SEQ ID NO: 1,
wherein administering the composition promotes increased vascularization of the penile tissue, thereby treating erectile dysfunction in the subject.

2. The method of claim 1, wherein the composition further comprises a pharmaceutically acceptable carrier.

3. The method of claim 2, wherein the pharmaceutically acceptable carrier is saline.

4. The method of claim 2, wherein the pharmaceutically acceptable carrier is a hydrogel.

5. The method of claim 2, wherein the pharmaceutically acceptable carrier is a nanoparticle.

6. A method for inhibiting erectile dysfunction in a male subject undergoing prostate surgery comprising administering to the major pelvic ganglion of the subject an effective amount of a composition comprising a polypeptide having the amino acid sequence set forth in SEQ ID NO: 1,
wherein administering the composition promotes increased vascularization of the penile tissue at the time of surgery, thereby inhibiting erectile dysfunction in the subject.

7. The method of claim 6, wherein the composition further comprises a pharmaceutically acceptable carrier.

8. The method of claim 7, wherein the pharmaceutically acceptable carrier is saline.

9. The method of claim 7, wherein the pharmaceutically acceptable carrier is a hydrogel.

10. The method of claim 7, wherein the pharmaceutically acceptable carrier is a nanoparticle.

\* \* \* \* \*